(12) United States Patent
Bosnes

(10) Patent No.: US 8,110,351 B2
(45) Date of Patent: Feb. 7, 2012

(54) METHOD FOR ISOLATING NUCLEIC ACIDS AND PROTEIN FROM A SINGLE SAMPLE

(75) Inventor: Marie Bosnes, Oslo (NO)

(73) Assignee: Invitrogen Dynal AS, Oslo (NO)

( * ) Notice: Subject to any disclaimer, the term of this patent is extended or adjusted under 35 U.S.C. 154(b) by 357 days.

(21) Appl. No.: 10/501,162

(22) PCT Filed: Jan. 16, 2003

(86) PCT No.: PCT/GB03/00156
§ 371 (c)(1),
(2), (4) Date: Apr. 26, 2005

(87) PCT Pub. No.: WO03/062462
PCT Pub. Date: Jul. 31, 2003

(65) Prior Publication Data
US 2005/0239068 A1  Oct. 27, 2005

(30) Foreign Application Priority Data

Jan. 16, 2002 (GB) ................... 0200927.2
Nov. 21, 2002 (GB) ................... 0227239.1

(51) Int. Cl.
C12Q 1/68 (2006.01)
G01N 33/53 (2006.01)
C12M 1/34 (2006.01)
C12M 3/00 (2006.01)
C07H 19/00 (2006.01)
C07H 21/00 (2006.01)

(52) U.S. Cl. .... 435/6.1; 435/7.1; 435/287.1; 435/287.2; 536/22.2

(58) Field of Classification Search ............ 435/6.1, 435/7.1, 287.1, 287.2; 536/22.1
See application file for complete search history.

(56) References Cited

U.S. PATENT DOCUMENTS

| | | | |
|---|---|---|---|
| 873,102 A | 12/1907 | Sly | |
| 3,509,024 A | 4/1970 | Jurgens et al. | |
| 4,055,469 A | 10/1977 | Snoke et al. | |
| 4,336,173 A | 6/1982 | Ugelstad | |
| 4,379,843 A | 4/1983 | Cashion | |
| 4,384,933 A | 5/1983 | Takasaki | |
| 4,435,509 A | 3/1984 | Berthold et al. | |
| 4,459,378 A | 7/1984 | Ugelstad | |
| 4,648,975 A | 3/1987 | Barkatt et al. | |
| 4,654,267 A | 3/1987 | Ugelstad et al. | |
| 4,672,040 A | 6/1987 | Josephson | |
| 4,710,472 A | 12/1987 | Saur et al. | |
| 4,732,811 A | 3/1988 | Margel | |
| 4,772,550 A | 9/1988 | Greenquist | |
| 4,808,521 A | 2/1989 | Allen | |
| 4,843,012 A | 6/1989 | Bonville | |
| 4,861,705 A | 8/1989 | Margel et al. | |
| 4,871,433 A | 10/1989 | Wagner et al. | |
| 4,874,813 A | 10/1989 | Shannessy | |
| 4,889,916 A | 12/1989 | Packard et al. | |
| 4,897,444 A | 1/1990 | Brynes et al. | |
| 4,908,318 A | 3/1990 | Lerner | |
| 4,910,148 A | 3/1990 | Sorensen et al. | |
| 4,920,061 A | 4/1990 | Poynton et al. | |
| 366,438 A | 5/1990 | Gannon et al. | |
| 4,921,805 A | 5/1990 | Gebeyehu et al. | |
| 4,923,978 A | 5/1990 | McCormick | |
| 4,935,342 A | 6/1990 | Seligson et al. | |
| 4,950,712 A | 8/1990 | Letourneur et al. | |
| 4,952,519 A | 8/1990 | Lau | |
| 4,957,605 A | 9/1990 | Hurwitt et al. | |
| 4,997,932 A | 3/1991 | Reardon et al. | |
| 5,000,635 A | 3/1991 | Jensen et al. | |
| 5,019,416 A | 5/1991 | Honzawa | |
| 5,030,697 A | 7/1991 | Hugl et al. | |
| 5,032,281 A | 7/1991 | Nagamatsu et al. | |
| 5,053,326 A | 10/1991 | Renz | |
| 5,055,556 A | 10/1991 | Stryer et al. | |
| 5,057,426 A | 10/1991 | Henco et al. | |
| 5,075,430 A | 12/1991 | Little | |
| 5,076,950 A | 12/1991 | Ullman et al. | |
| 5,079,155 A | 1/1992 | Cox et al. | |
| 5,084,169 A * | 1/1992 | Noble et al. | ........... 210/222 |
| 5,124,444 A | 6/1992 | Van Ness et al. | |
| 5,126,028 A | 6/1992 | Hurwitt et al. | |
| 5,128,247 A | 7/1992 | Koller | |

(Continued)

FOREIGN PATENT DOCUMENTS

AU      27636/88      9/1989

(Continued)

OTHER PUBLICATIONS

Riol et al, Optimized lymphocyte protein extraction performed simultaneously with DNA and RNA isolation: Application to the study of factors affecting DNA, RNA and protein recovery from lymphocytes of the oldest individuals. Analytical Biochemistry 1999, 275, 192-201.*

Schubler et al, Combined isolation of nucleic acids and protein from small amounts of tissue, 1995, TIG, 11, 378-379.*

Safarik et al, Biologically active compounds and Xenobiotics: magnetic affinity separations, 2000, (Editors: Allen et al, Academic Press), 2000, pp. 2163-2170.*

Oswald et al, Differential biogenesis of photosystem -II in mesophyll, 1990, Eur. J. Biochem., 190, 185-194.*

Beherns et al, The charge of glass and silica surfaces, 2001, Journal of Chemical Physics, 115, 6716-6721.*

Haukanes et al, Application of magnetic beads in Bioassay, Nature, Biotechnology, 1993, 11, pp. 60-63.*

(Continued)

Primary Examiner — Stephen Kapushoc
Assistant Examiner — Narayan Bhat

(57) ABSTRACT

The present invention comprises a method of isolating nucleic acid and protein from the same sample with solid supports, wherein nucleic acid and protein components contained in the sample become bound to distinct solid supports. The invention also allows for kits for isolating nucleic acid and protein from the same sample and for use of the method of isolating nucleic acid and protein for the analysis and/or comparison of mRNA and/or protein expression and/or their correlation to genomic information.

28 Claims, 14 Drawing Sheets

U.S. PATENT DOCUMENTS

| | | | |
|---|---|---|---|
| 5,155,018 A | 10/1992 | Gillespie et al. |
| 5,183,809 A | 2/1993 | Weisz et al. |
| 5,204,246 A | 4/1993 | Jhingan |
| 5,234,809 A | 8/1993 | Boom et al. |
| 5,234,824 A | 8/1993 | Mullis |
| 5,234,924 A | 8/1993 | Taverne et al. |
| 5,296,347 A | 3/1994 | LaMotte |
| 5,329,000 A | 7/1994 | Woodard et al. |
| 5,334,499 A | 8/1994 | Burdick et al. |
| 5,342,931 A | 8/1994 | Woodard et al. |
| 5,433,847 A | 7/1995 | Rice |
| 5,434,270 A | 7/1995 | Ponticello et al. |
| 5,434,279 A | 7/1995 | Wimmer |
| 5,455,157 A | 10/1995 | Hinzpeter et al. |
| 5,491,223 A | 2/1996 | Okamoto |
| 5,503,816 A | 4/1996 | Woodard et al. |
| 5,508,164 A | 4/1996 | Kausch et al. |
| 5,510,084 A | 4/1996 | Cros et al. |
| 5,512,439 A * | 4/1996 | Hornes et al. ............... 435/6 |
| 5,523,231 A | 6/1996 | Reeve |
| 5,538,872 A | 7/1996 | Bahl et al. |
| 5,582,988 A | 12/1996 | Backus et al. |
| 5,596,092 A | 1/1997 | Schneider |
| 5,599,667 A | 2/1997 | Arnold et al. |
| 5,612,473 A | 3/1997 | Wu et al. |
| 5,616,467 A | 4/1997 | Olsen et al. |
| 5,622,822 A | 4/1997 | Ekeze et al. |
| 5,625,054 A | 4/1997 | Woodard et al. |
| 5,631,146 A | 5/1997 | Szostak et al. |
| 5,641,628 A | 6/1997 | Bianchi |
| 5,652,348 A | 7/1997 | Burton et al. |
| 5,654,179 A | 8/1997 | Lin |
| 5,660,984 A | 8/1997 | Davis et al. |
| 5,672,659 A | 9/1997 | Shalaby et al. |
| 5,677,199 A | 10/1997 | Arrhenuis |
| 5,696,251 A | 12/1997 | Arnold et al. |
| 5,705,628 A | 1/1998 | Hawkins |
| 5,710,028 A | 1/1998 | Eyal et al. |
| 5,711,915 A | 1/1998 | Siegmund et al. |
| 5,762,903 A | 6/1998 | Park et al. |
| 5,770,712 A | 6/1998 | Roy et al. |
| 5,780,319 A | 7/1998 | Maxfield et al. |
| 5,797,202 A | 8/1998 | Akesaka |
| 5,807,527 A | 9/1998 | Burgoyne |
| 5,843,663 A | 12/1998 | Stanley et al. |
| 5,874,221 A | 2/1999 | Tooley et al. |
| 5,898,071 A | 4/1999 | Hawkins |
| 5,907,016 A | 5/1999 | Velander et al. |
| 5,914,367 A | 6/1999 | Dordick et al. |
| 5,916,746 A | 6/1999 | Cobbs et al. |
| 5,945,520 A | 8/1999 | Burton et al. |
| 5,945,525 A | 8/1999 | Uematsu et al. |
| 5,958,788 A | 9/1999 | Johnson et al. |
| 5,962,412 A | 10/1999 | Hogan, Jr. |
| 5,981,235 A | 11/1999 | Shultz et al. |
| 5,981,735 A | 11/1999 | Thatcher et al. |
| 6,010,867 A | 1/2000 | Kobayashi et al. |
| 6,027,945 A | 2/2000 | Smith et al. |
| 6,051,380 A | 4/2000 | Sosnowski et al. |
| 6,060,246 A | 5/2000 | Summerton et al. |
| 6,090,288 A | 7/2000 | Berglund et al. |
| 6,113,906 A | 9/2000 | Greenwald et al. |
| 6,120,985 A * | 9/2000 | Laugharn et al. ......... 435/1.3 |
| 6,194,562 B1 | 2/2001 | Smith et al. |
| 6,203,768 B1 | 3/2001 | McCormick et al. |
| 6,207,381 B1 | 3/2001 | Larsson et al. |
| 6,218,531 B1 * | 4/2001 | Ekenberg ............... 536/25.41 |
| 6,255,477 B1 * | 7/2001 | Kleiber et al. ............. 536/25.4 |
| 6,270,970 B1 | 8/2001 | Smith et al. |
| 6,284,470 B1 | 9/2001 | Bitner et al. |
| 6,287,765 B1 | 9/2001 | Cubicciotti |
| 6,310,199 B1 * | 10/2001 | Smith et al. ............. 536/25.4 |
| 6,342,387 B1 | 1/2002 | Hayashizaki et al. |
| 6,365,362 B1 | 4/2002 | Terstappen et al. |
| 6,368,800 B1 | 4/2002 | Smith et al. |
| 6,406,913 B1 | 6/2002 | Ullman et al. |
| 6,440,748 B1 | 8/2002 | Katerkamp et al. |
| 6,448,091 B1 | 9/2002 | Massey et al. |
| 6,473,586 B2 | 10/2002 | Noda et al. |
| 6,489,160 B2 | 12/2002 | Hashimoto |
| 6,534,262 B1 | 3/2003 | McKernan |
| 6,545,151 B2 | 4/2003 | Terasawa et al. |
| 6,562,573 B2 | 5/2003 | Halaka |
| 6,582,907 B1 | 6/2003 | Epps et al. |
| 6,627,748 B1 | 9/2003 | Ju et al. |
| 6,635,420 B1 | 10/2003 | Hosel et al. |
| 6,645,733 B1 | 11/2003 | Daksis et al. |
| 6,660,533 B2 | 12/2003 | Mallet et al. |
| 6,677,164 B1 | 1/2004 | Thoma et al. |
| 6,723,510 B2 * | 4/2004 | Lubenow et al. ................. 435/6 |
| 6,743,586 B2 | 6/2004 | Marino et al. |
| 6,811,973 B1 | 11/2004 | Reich |
| 6,811,980 B2 | 11/2004 | Ford |
| 6,818,394 B1 | 11/2004 | O'Donnell-Maloney et al. |
| 6,833,257 B2 | 12/2004 | Lee et al. |
| 6,881,536 B1 | 4/2005 | Shah et al. |
| 6,914,137 B2 | 7/2005 | Baker |
| 6,919,200 B2 * | 7/2005 | Ibrahim ....................... 435/270 |
| 6,956,077 B1 | 10/2005 | Akiyama et al. |
| 6,969,603 B2 | 11/2005 | Hayashizaki et al. |
| 7,018,610 B2 | 3/2006 | Hunter et al. |
| 7,056,682 B2 | 6/2006 | Kamei et al. |
| 7,078,536 B2 | 7/2006 | Ge et al. |
| 7,122,659 B2 | 10/2006 | Nikiforov |
| 7,173,124 B2 | 2/2007 | Deggerdal et al. |
| 7,183,116 B2 | 2/2007 | Aebersold et al. |
| 7,262,006 B1 | 8/2007 | Belly et al. |
| 7,338,805 B2 | 3/2008 | Bourget et al. |
| 2001/0018513 A1 | 8/2001 | Baker |
| 2002/0009744 A1 | 1/2002 | Bogdanov |
| 2002/0025572 A1 | 2/2002 | Hayashizaki et al. |
| 2002/0058278 A1 | 5/2002 | Stefano et al. |
| 2002/0164674 A1 | 11/2002 | Tsien et al. |
| 2002/0182169 A1 | 12/2002 | Hunter et al. |
| 2003/0044777 A1 | 3/2003 | Beattie |
| 2003/0099954 A1 | 5/2003 | Miltenyi et al. |
| 2003/0124742 A1 | 7/2003 | Prakash |
| 2003/0130499 A1 | 7/2003 | Baker |
| 2003/0199078 A1 | 10/2003 | Kleiber et al. |
| 2003/0211508 A1 | 11/2003 | Ge et al. |
| 2003/0229013 A1 | 12/2003 | Wu et al. |
| 2004/0009506 A1 | 1/2004 | Stephan et al. |
| 2004/0077019 A1 | 4/2004 | Gstach |
| 2004/0092449 A1 | 5/2004 | Ekwuribe |
| 2004/0152084 A1 | 8/2004 | Slattum et al. |
| 2004/0219556 A1 | 11/2004 | Bazan et al. |
| 2004/0259082 A1 | 12/2004 | Williams |
| 2005/0123932 A1 | 6/2005 | Astatke |
| 2006/0035208 A1 | 2/2006 | Roget et al. |
| 2006/0036028 A1 | 2/2006 | Moody et al. |
| 2006/0194202 A1 | 8/2006 | Schatz et al. |
| 2006/0204584 A1 | 9/2006 | Harper et al. |
| 2006/0263780 A1 | 11/2006 | Baker et al. |
| 2007/0117972 A1 | 5/2007 | Halaka |
| 2007/0190559 A1 | 8/2007 | Deggerdal et al. |
| 2007/0231892 A1 | 10/2007 | Baker |
| 2008/0261202 A1 | 10/2008 | Baker et al. |
| 2008/0293035 A1 | 11/2008 | Bergholtz et al. |
| 2008/0300396 A1 | 12/2008 | Deggerdal et al. |
| 2008/0305528 A1 | 12/2008 | Baker |
| 2009/0068724 A1 | 3/2009 | Deggerdal et al. |
| 2009/0149646 A1 | 6/2009 | Deggerdal et al. |

FOREIGN PATENT DOCUMENTS

| | | |
|---|---|---|
| CA | 2157968 | 3/1996 |
| DE | 42 37 381 C1 | 11/1992 |
| DK | 4038293 | 6/1992 |
| DK | 3639949 | 1/1999 |
| EP | 106873 | 11/1983 |
| EP | 0254616 | 1/1988 |
| EP | 281390 | 9/1988 |
| EP | 0301899 | 2/1989 |
| EP | 0338591 | 10/1989 |
| EP | 0268946 A3 | 3/1990 |
| EP | 270017 | 3/1990 |
| EP | 0270017 A3 | 3/1990 |
| EP | 0281390 A3 | 4/1990 |

| | | |
|---|---|---|
| EP | 366438 | 5/1990 |
| EP | 0368092 | 5/1990 |
| EP | 0167488 | 7/1990 |
| EP | 0389063 | 9/1990 |
| EP | 276138 | 4/1991 |
| EP | 0512767 | 11/1992 |
| EP | 0515484 | 12/1992 |
| EP | 4139664 | 6/1993 |
| EP | 0268946 | 9/1993 |
| EP | 416748 | 3/1994 |
| EP | 0707077 | 4/1996 |
| EP | 0832897 | 4/1998 |
| EP | 834729 | 4/1998 |
| EP | 0853123 | 7/1998 |
| EP | 0 885 958 A1 | 12/1998 |
| EP | 0897978 | 2/1999 |
| EP | 1069131 | 1/2001 |
| EP | 502589 | 9/2001 |
| EP | 114506 | 8/2004 |
| GB | 200927.2 | 3/1982 |
| GB | 227239.1 | 5/1994 |
| GB | 9425138.6 | 2/1995 |
| GB | 2282138 | 3/1995 |
| JP | 63154696 | 6/1988 |
| JP | 1125395 | 5/1989 |
| JP | 2289596 | 11/1990 |
| JP | 8173194 | 7/1996 |
| JP | 10057056 | 3/1998 |
| JP | 11-501504 | 2/1999 |
| JP | 2001231907 | 8/2001 |
| JP | 2001518284 | 10/2001 |
| JP | 2006500050 | 1/2006 |
| WO | WO-86/00139 | 1/1986 |
| WO | WO-86/05815 | 10/1986 |
| WO | WO-88/09201 | 12/1988 |
| WO | WO-90/04019 | 4/1990 |
| WO | WO-90/06042 | 6/1990 |
| WO | WO-90/08159 | 7/1990 |
| WO | WO-90/14891 | 12/1990 |
| WO | WO-91/07660 | 5/1991 |
| WO | WO-91/08308 | 6/1991 |
| WO | WO 91/12079 | 8/1991 |
| WO | WO 92/17609 * | 10/1992 |
| WO | WO-93/03167 | 2/1993 |
| WO | WO-93/25709 | 12/1993 |
| WO | WO-93/25912 | 12/1993 |
| WO | WO-94/08239 | 4/1994 |
| WO | WO-94/11103 | 5/1994 |
| WO | WO-95/13368 | 5/1995 |
| WO | WO-95/27718 | 10/1995 |
| WO | WO-96/00228 | 1/1996 |
| WO | WO-96/08500 | 3/1996 |
| WO | WO-96/09116 | 3/1996 |
| WO | WO 96/18731 | 6/1996 |
| WO | WO-96/18731 | 6/1996 |
| WO | WO-96/18732 | 6/1996 |
| WO | WO-96/36706 | 11/1996 |
| WO | WO-96/41810 | 12/1996 |
| WO | WO-96/41811 | 12/1996 |
| WO | WO-97/10331 | 3/1997 |
| WO | WO-97/28171 | 8/1997 |
| WO | WO-97/29825 | 8/1997 |
| WO | WO-97/31105 | 8/1997 |
| WO | WO-97/36004 | 10/1997 |
| WO | WO-98/51693 | 11/1998 |
| WO | WO-99/22020 | 5/1999 |
| WO | WO-99/22021 | 5/1999 |
| WO | WO-99/29703 A2 | 6/1999 |
| WO | WO 00/29848 | 5/2000 |
| WO | WO 00/42432 | 7/2000 |
| WO | WO-00/44928 | 8/2000 |
| WO | WO-00/49031 | 8/2000 |
| WO | WO-00/58329 | 10/2000 |
| WO | WO 00/61806 * | 10/2000 |
| WO | WO-00/65041 | 11/2000 |
| WO | WO-00/69872 | 11/2000 |
| WO | WO-00/70040 | 11/2000 |
| WO | WO-00/70041 | 11/2000 |
| WO | WO-01/94572 | 12/2001 |
| WO | WO02/10373 | 2/2002 |
| WO | WO-02/16580 | 2/2002 |
| WO | WO-02/48164 | 6/2002 |
| WO | WO03/062462 | 7/2003 |
| WO | WO-2004/055213 | 7/2004 |
| WO | WO-2006/018731 | 2/2006 |

OTHER PUBLICATIONS

K. Büssow, et al., "A Method for Global Protein Expression and Antibody Screening on High-Density Filters of an Arrayed cDNA Library," *Nucleic Acids Research*, 1998, vol. 26, No. 21, pp. 5007-5008.
Abramson, R. et al., Current Opinion in Biotechnology (1993) 4(1): 41-47.
Bitner, R. et al., Proceedings of SPIE (2000) 3926: 126-133.
Cordes, R et al., Biotechnology Progress (1990) 6(47): 283-285.
Database WPI, Derwent Publications Ltd. London, GB; AN (1991) 077588, XP002295078 & SU 1 638 162 A (as SIBE Cytology).
De Latour, C et al., IEEE Transactions on Magnetics (1975) 11: 1570-1572.
Eberwine, J. et al., Biotechniques (1996) 4: 584-591.
Fellmann, F. et al., Biotechniques (1996) 21(5): 766,768 & 770.
Fluka Catalog, , "p. 1394", Fluka Catalog (1995/1996) 1394.
Freifelder, D., Physical Biochemistry (1982) 216-275, 2nd E.
Invitrogen, "Dynabeads Epithelial Enrich", http://tools.invitrogen.com/content/sfs/manuals/16102-Dynabeads-Epithelial-Enrich-(rev004).pdf (2006) (4): 1-2.
Invitrogen, "Dynal Magnetic Beads aka Dynabeads", http://www.invitrogen.com/site/us/en/home/brands/Dynal.html (2008) 1-4.
Invitrogen, "MSDS Dynabeads M-270 Streptavidin", https://tools.invitrogen.com/content/sfs/msds/DYNABEADS%20M270%20STREPTAVIDIN_MTR-NAIV_EN.pdf (Jan. 17, 2008) 1-5.
JP 98-210396, "Abstract", XP-002106739.
Kothari, et al., J. Chromatography (1972) 73: 449-462.
Li, Fusheng et al., Chinese Journal of Biotechnology (1997) 13 (1): 37-42.
Lu, T. et al., Journal of Chromatography (1994) A 686:339-343.
McLaughlin, Larry W., Chemical Reviews (1989) 89 (2): 309-319.
Millard, Fiona et al., Journal of Chromatography (4/91975) 107(1): 125-140.
Natarajan, G. et al., Analytical Biochemistry (May 15, 1996) 237 (1): 152-155.
Peterson, et al., Biochemistry (1969) 8(7): 2916-2923.
Reeck, Gerald R. et al, Proceedings of the National Academy of Sciences (PNAS) (Aug. 15, 1972) 69(8): 2317-2321.
Slaby, Ivan et al., Protein Expression and Purification (Aug. 1991) 2(4): 270-277.
Yolken, Robert H. et al., Molecular and Cellular Probes (1991) 5: 151-156.
CA Application No. 2,473,376, Office Action mailed Aug. 12, 2010.
CA Application No. 2,473,376, Response to Aug. 12, 2010 Office Action filed Feb. 11, 2011.
CN Application No. 03802373.3, Office Action mailed Jan. 6, 2011.
CN Application No. 03802373.3, Response to Jan. 6, 2011 Office Action filed Apr. 20, 2011.
CN Application No. 03802373.3, Response to Office Action filed Feb. 25, 2010.
EP Application No. 03700880.2, Examination Report mailed Feb. 25, 2008.
EP Application No. 03700880.2, Response to Feb. 25, 2008 Office Action filed Sep. 4, 2008.
JP Application No. 2003-562329, Office Action mailed Oct. 28, 2009.
JP Application No. 2003-562329, Office Action mailed Sep. 1, 2008.
JP Application No. 2003-562329, Response to Office Action filed Mar. 2, 2009.

* cited by examiner

Summary of model system

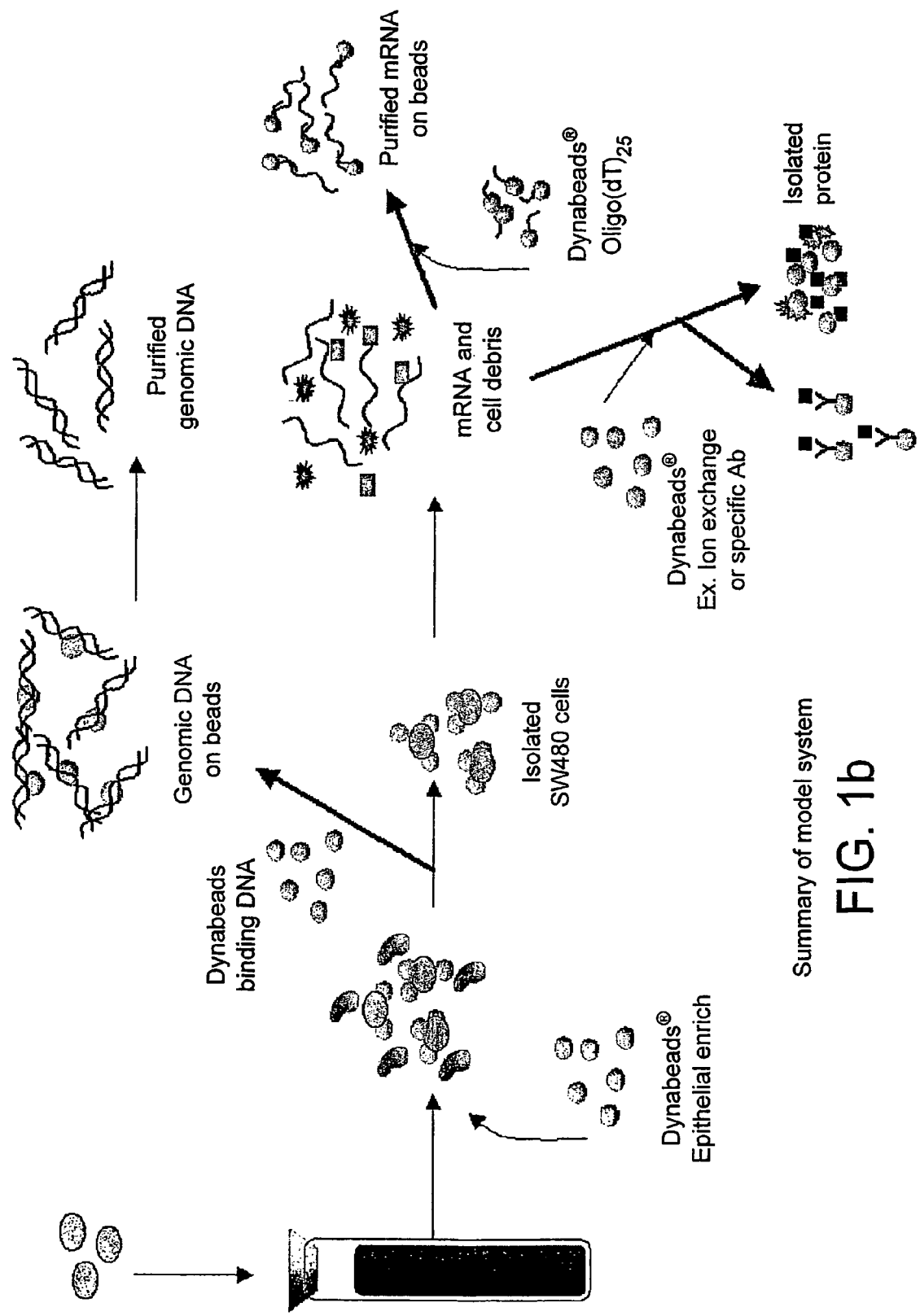
FIG. 1b Summary of model system

Re-use of Solid-phase cDNA library in multiple PCR experiments, detecting different transcripts Cultured Carcinoma Cells

| Lane | No. of cells | Amplicon | Round of PCR |
|---|---|---|---|
| 1 | 10000 | ESX | first (45 cycles) |
| 2 | 10000 | Mucin1 | second (45 cycles) |
| 3 | 10000 | CK19 | third (30 cycles) |
| 4 | 10 | CK19 | first (nested) |
| 5 | 10 | ESX | second (nested) |

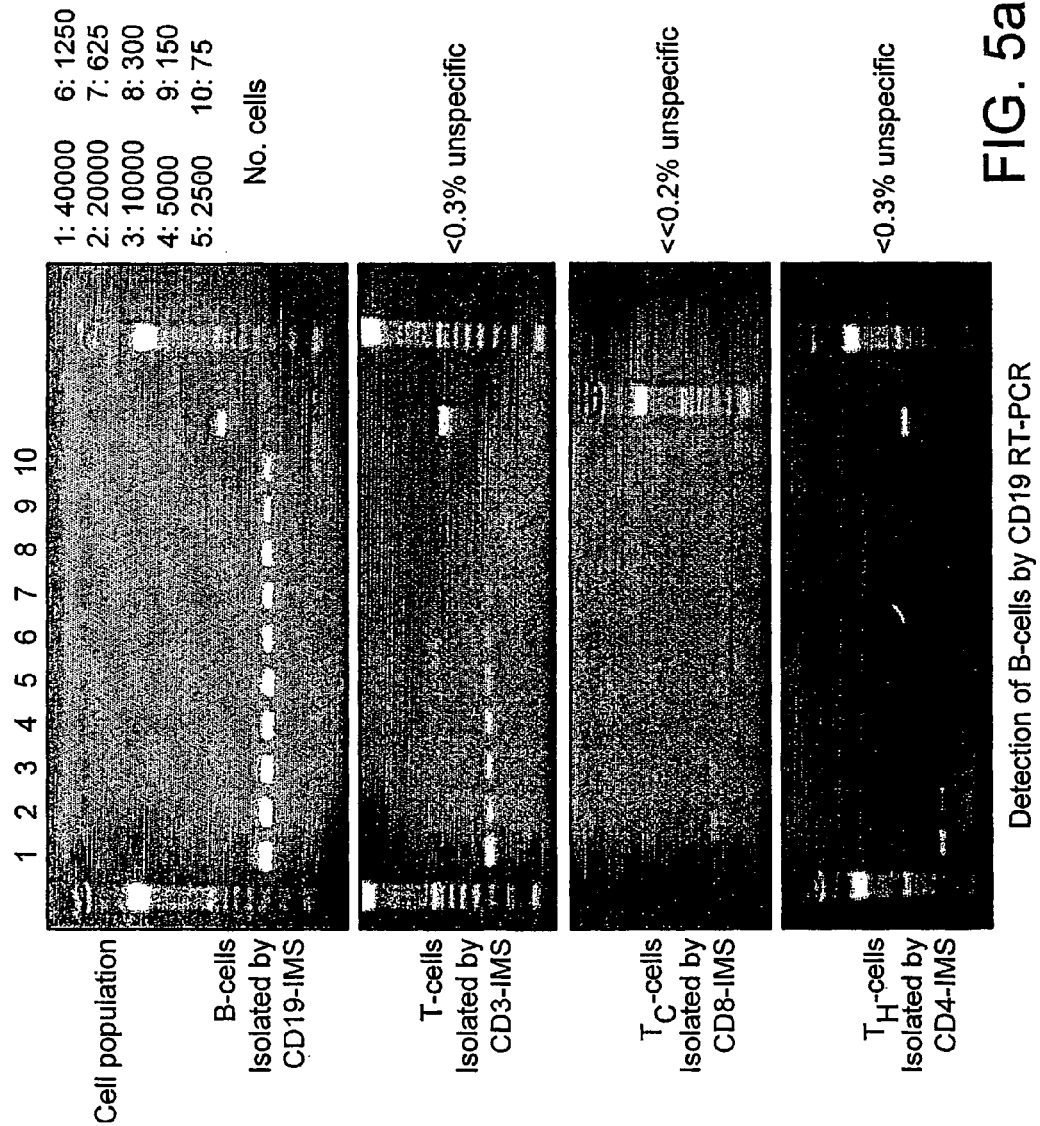

Integrity of isolated DNA:
No degradation

METHOD FOR ISOLATING NUCLEIC ACIDS AND PROTEIN FROM A SINGLE SAMPLE

This is the U.S. National Phase under 35 U.S.C. §371 of International Application PCT/GB03/00156, filed Jan. 16, 2003, which claims priority to Great Britain Patent Application Nos. 0200927.2, filed Jan. 16, 2002 and 0227239.1, filed Nov. 21, 2002.

The present invention relates to a method of analysing a single sample for DNA, mRNA and protein expression. This is advantageous in correlating information relating to both mRNA and protein expression to genomic information.

The human genome is now more or less mapped and the gene number has been found to be much lower than first estimated. This shows that human complexity does not lie in the number of genes, but in how the genes are utilized and gene products combined and modified. Thus, the focus on studying the gene products and their interaction has become more significant.

It is known that only a fraction of the genes are transcribed in a single cell or cell type, and that one gene can give rise to many different proteins. This is partly due to alternative reading frames, alternative translational start/stop codons and alternative splicing of mRNA. It is also known that the relative quantitative levels of mRNA and protein do not always- or seldom correspond. One mRNA species can also give rise to different proteins because of post-translational modifications.

Thus an individual's genome (the collection of all genes), can be regarded as representing the genetic "possibilities" of an individual, while the transcriptome (the collection of mRNAs transcribed from the genome) represents what might possibly happen. The proteome, however (i.e. the total collection of all proteins translated from the transcriptome and modified post-translationally) represents reality, i.e. what really happened.

Accordingly, all three levels, DNA, RNA and protein, give information which is valuable for different reasons. The DNA or genotype gives important information about genetic predispositions and acquired mutations/local rearrangements. Both mRNA and protein profiles generate "molecular portraits" of a biological state/stage or disease, and may also be used for staging and monitoring of the disease development and treatment. As opposed to the DNA, both mRNA and protein profiles represent "snap shots" of the cell's biology, since they are continuously changing in response to the surrounding environment. Due to regulatory mechanisms acting both at the transcriptional, translational and post-translational levels, mRNA and protein levels do not always correlate. It is therefore crucial to study both mRNA and protein from the same sample.

Thus, as mentioned above, there is however not necessarily a 1:1 correlation between mRNA and protein levels. If protein levels and corresponding mRNA levels are compared, then for every protein for which the ratio of mRNA and protein is not 1:1 then this protein is subject to some form of interesting post transcriptional and/or post translational regulation. mRNA/protein ratios for specific genes are often shifted during disease conditions. To be able to study regulatory mechanisms and to unravel the reasons behind such a shift in mRNA/protein ratios, it is crucial to isolate mRNA and protein from the same sample. A novel and advantageous method for carrying out such isolation is presented herein.

Variation in protein or mRNA levels between individuals, for example in an individual with a disease state compared with a "normal" patient, are often due to single nucleotide polymorphisms (SNPs) or other forms of mutation or genetic predisposition in their genes (i.e. their DNA) or their regulatory regions. For this reason it is advantageous to be able to isolate DNA and protein, preferably DNA, RNA and protein, and especially DNA, mRNA and protein from the same sample to enable direct comparison. Such methods are also provided by the present invention.

In particular, it has now been found that nucleic acid and protein, and in particular DNA, RNA and protein can be isolated from a single sample in a form suitable for downstream manipulation and analysis, by a simple and easy to perform procedure. This isolation method involves binding nucleic acid and protein or preferably DNA, RNA and protein from the same sample on to distinct solid supports or areas of solid supports so that the isolated components can be analysed separately. Advantageously these methods can be combined with a further initial step involving the specific isolation of one or more particular cell types or populations (e.g. B-cells, T-cells, monocytes) from the sample before the isolation of nucleic acid and protein is carried out. In particular, it has been shown that DNA (e.g. genomic DNA), RNA (e.g. mRNA) and proteins may be isolated from a single sample with a high, documented purity. Different cell populations can also be isolated sequentially from the same sample and then each of these can be subjected to DNA, RNA and protein isolation.

In one aspect, the present invention thus provides a method of isolating nucleic acid and protein from the same sample, said method comprising contacting said sample with solid supports, whereby the nucleic acid and protein components in said sample become bound to distinct solid supports.

The nucleic acid to be isolated may be DNA, RNA or any naturally occurring modification thereof, and combinations thereof. Thus, the entire nucleic acid based component of a sample can be isolated in the method of the invention. In a preferred embodiment of the invention however DNA and/or RNA are separately isolated from the same sample onto distinct solid supports.

Thus, in preferred embodiments the present invention provides a method of isolating RNA and protein or DNA and protein from the same sample. In especially preferred embodiments the invention provides a method of isolating DNA, RNA and protein from the same sample.

In embodiments and steps of the methods of the invention, where the nucleic acid to be isolated from the sample is DNA, preferably the DNA is genomic DNA (gDNA) and may be in a single or double stranded or in any other form. In certain embodiments a specific DNA molecule, e.g comprising a gene encoding a specific protein may be isolated.

In embodiments and steps of the methods of the invention, where the nucleic acid to be isolated from the sample is RNA, total RNA may be isolated or a particular form or subset of RNA may be isolated. In preferred embodiments of the invention mRNA is isolated from the sample. In certain embodiments a specific RNA molecule, e.g. a specific mRNA encoding a specific protein may be isolated.

In the methods of the present invention described herein the steps of isolating nucleic acid and protein onto distinct solid phases involving contacting the sample with said solid phases can be carried out sequentially or simultaneously. Similarly, in embodiments where it is desired to isolate protein, DNA and RNA as separate components then these isolations can be carried out in the same step or in separate sequential steps. As will be described further below, in certain situations it may be desirable to carry out protein and nucleic acid (e.g. DNA and/or RNA) isolations on separate aliquots (or fractions) of the same sample (i.e. on a divided or split sample). In such cases the isolations may be carried out in parallel steps, e.g. simultaneously in parallel.

Preferably the required isolations are carried out in separate sequential steps which can, in turn, be carried out in any order. Thus, although in the preferred embodiments of the invention DNA is isolated in a first step, followed by RNA in a second step and protein in a third step the different components can be isolated in any order.

The term "distinct solid phases" as used herein includes the use of different solid supports (i.e. supports with different binding and surface properties) in different steps of the method of the invention (for example in embodiments where sequential steps are used to bind the desired nucleic acid components and proteins), different supports added in same step (for example in embodiments where the isolation of the desired nucleic acid components and protein are carried out in the same step) and the use of supports with the same surface properties added in different steps, where binding of a particular nucleic acid or protein component is enabled by virtue of different incubation conditions. Furthermore, in some situations a particular solid support may bind different components (e.g. protein and nucleic acid, or cells and protein or nucleic acid etc.) when placed under different conditions e.g. different incubation conditions, reagents, environment etc. Such differences may also be exploited to bind different components to the same solid support, but in distinct or different steps, e.g. at different stages of the procedure, such that the desired components may be separately isolated. This term also includes different areas of a single solid support, which may for example be designed to have different surface properties such that particular nucleic acid and protein components bind to different areas or different ligands of the same support.

As mentioned above, it is an important aspect of the invention that nucleic acid and protein are analysed from the same sample.

"Same sample" as used herein refers to the isolation of the appropriate nucleic acid and protein components from a single, i.e. undivided sample. In this way the method of the invention is distinguished from prior art methods which may involve obtaining multiple samples or equivalent procedures, for example obtaining one initial sample, and straightaway at the outset dividing it into aliquots e.g. obtaining a sample and dividing it into aliquots on which a separate analysis of DNA, RNA and protein (one for each aliquot) is carried out and the results compared. Thus, an "undivided sample" may be viewed as a sample which is not divided straightaway e.g. immediately or initially after sampling, or at the outset before any isolation procedures are carried out. Thus, subsequent later division of the sample is not precluded, but it is not divided initially, or as a first step in the sample treatment process. Conveniently, as will be described further below, prior to carrying out nucleic acid and/or protein isolation procedures, it may be advantageous, or desirable first to isolate a particular desired population or sub-population of cells, or indeed to isolate all (or substantially all) the cells or any desired fraction thereof from the sample, and/or to lyse the cells in the sample or in any isolated population or fraction thereof. In such situations it may be desired or convenient to divide the single (i.e. same) sample after the cell isolation or cell lysis steps have been carried out.

Thus, division of the sample after an initial, or first, isolation step, or after two or more isolation steps is contemplated. This may be desirable if, for example, if it is desired to change conditions (e.g. ionic strength, salt concentration etc), e.g. to isolate different components. Thus, for example, protein and nucleic acid components (i.e. DNA and/or RNA) may be isolated from different aliquots of the sample after such a sample splitting or division-step. However, in one advantageous embodiment of the invention, the method is carried out using a single sample which is not divided at any stage or at any time. The fact that the multiple analysis of DNA, RNA and protein can be carried out on a single, undivided sample using the methods of the present invention is clearly advantageous and will allow for a more direct and accurate comparison between the various nucleic acid and protein components of the sample.

The samples suitable for use in the methods of the present invention may be any material containing nucleic acid and protein, including for example foods and allied products, clinical and environmental samples. However, the sample will generally be a biological sample, which may contain any viral or cellular material, including all prokaryotic or eukaryotic cells, viruses, bacteriophages, mycoplasmas, protoplasts and organelles. Such biological material may thus comprise all types of mammalian and non-mammalian animal cells, plant cells, algae including blue-green algae, fungi, bacteria, protozoa etc. Representative samples thus include whole blood and blood-derived products such as plasma, serum and buffy coat, bone marrow and samples obtained from other haematopoietic tissues, urine, faeces, cerebrospinal fluid or any other body fluids, tissues (for example solid tissues), cell cultures, cell suspensions etc. Preferably the sample is a live (e.g. a non-fixed sample), i.e. comprises viable cells, or at least cells which have not been treated in any way.

The sample may be freshly obtained, or stored or treated in any desired or convenient way, for example by dilution, or adding buffer, or other solutions or solvents, enzyme-containing solutions etc.), as long as the integrity of the nucleic acids and proteins, or the cells or other entities containing such nucleic acids and proteins within the original sample are maintained, i.e. are not substantially degraded. Nucleic acids and protein may be denatured but not degraded.

It is further advantageous that a crude sample can be taken directly from its source, e.g. directly from a patient or from the environment (e.g. a direct clinical or environmental sample) and its protein and nucleic acid analysed using the methods of the invention.

The nucleic acid- and protein-containing sample may, generally speaking, simply be contacted with the appropriate solid supports under conditions whereby the nucleic acids or proteins as appropriate will become bound to the solid support. If necessary, e.g. if the nucleic acid and protein to be isolated is not available for binding within the initial sample e.g. is contained within a biological particle as described above e.g. a viral coat or a cell membrane or wall, the initial binding step may be preceded by one or more separate steps to free the nucleic acid and protein components, e.g. by disrupting structural components such as cell walls or to achieve lysis. Procedures for achieving this are well known in the art. Thus, for example, although some cells e.g. blood cells, may be lysed by reagents such as detergent alone, other cells, e.g. plant or fungal cells or solid animal tissues may require more vigorous treatment such as, for example, grinding in liquid nitrogen, heating in the presence of detergent, alkaline lysis in the presence of detergent. The main requirement is that procedures for freeing the nucleic acid and protein are chosen such that the particular nucleic acid and protein species which are to be isolated in the methods of the invention remain sufficiently intact, e.g. are not substantially degraded.

Preferably samples are 10 µl to 100 ml in size, preferably from 200 µl to 10 ml. The method of the invention may be used for small samples, e.g. less than 1 ml or for larger samples e.g. at least 2 ml, e.g. more than 5 ml or 10 ml or 50 ml. A major advantage of the present invention is that small sample volumes may be used, and in particular that protein may be isolated from such small sample volumes following, or concurrently with, DNA and/or RNA isolation. This feature makes the method of the invention particularly suitable for automation. Advantageously the sample volume as subjected to the nucleic acid/protein isolation procedures is 1 ml or less, e.g. 10 to 800 µl, e.g. 20 to 500 µl, or 50 to 200 µl. For example, the method may be performed on a sample containing $1\times10^4$ to $1\times10^6$ cells, preferably $1\text{-}10\times10^5$ cells. The method described is highly scalable and can be used to detect DNA/RNA/protein in 1, 5, 10, 20, 200 or 2000 or more cells.

As mentioned above an optional and preferred initial step once the sample has been obtained is to enrich the sample for particular populations, e.g. particular populations of cells or organelles for which the nucleic acid and protein is to be analysed.

Methods of enrichment are well known and documented in the art. Preferred methods involve the use of a solid phase, i.e. the binding of the population(s) in question to a solid phase and exemplary methods will be discussed in more detail below. In such methods, one or more steps of positive and/or negative solid phase selection can be used, as appropriate, depending on the desired purity of sub-population required. Such techniques are well known and described in the art. Briefly, in a negative selection step, the cells/populations which bind to the solid phases are removed from the sample to be analysed, whereas in a positive selection step the cells/populations which bind to the solid phases are retained in the sample to be analysed.

Exemplary and preferred antibodies for use in the isolation of specific cell populations are CD15 and CD45 antibodies (specific for leukocytes), CD14 antibodies (specific for monocytes), CD2, CD3, CD4 and CD8 antibodies (specific for T-cells), CD19 antibodies (specific for B-cells) and Anti Ber EP4 antibodies (specific for epithelial cells and in particular circulating carcinoma cells). Other antigens may also be used as the basis for detection by binding to specific antibodies (or antibody fragments, derivatives etc.), as indeed may any other cell surface molecule which may bind specifically to a binding partner or ligand.

If desired, prior to cell lysis, cell surface proteins may be subjected to an in vitro modification procedure for example chemical modification, e.g. biotinylation or radiolabelling, for example to introduce a label or reporter or marker group etc., prior to nucleic acid and protein isolation steps. Such modified surface proteins may then be isolated by a specific or adapted isolation procedure. Thus, for example, a biotinylated surface (e.g. membrane) protein may be isolated by binding to a solid support carrying streptavidin or avidin.

Other methods of isolating a desired cell population may also be used, as desired, for example Laser Capture Microdissection.

Where the method of the invention involves such a preliminary cell/organelle etc. isolation step, it will be appreciated that larger sample volumes may be used, e.g. 1-50 ml, e.g. 2 to 20 ml or 5-10 ml, for example of a blood or other clinical sample.

Sample preparation is one of the bottlenecks in proteomics in that due to the variation in abundancy and lack of specific amplification technology for proteins, it is advantageous to reduce sample complexity in order to increase resolution. Thus the optional step of the present invention by which a particular sample can be treated to specifically enrich for a particular specific population or populations of cells, organelles, etc., and thereby proteins is extremely advantageous. Thus, it can be seen that the methods of the invention allow the enrichment of a particular population of cells and the analysis of DNA, RNA and protein therefrom using the same single sample. The fact that this sample can be taken directly from a patient is a further advantage.

The feature of specifically or selectively isolating a desired population may be applied advantageously to comparing multiple (e.g. 2 or more, e.g. 2 to 10 or 2 to 6) populations from the same sample. Thus, for example, by the use of different appropriate binding partners specific for particular desired populations and coupled to different solid supports, different populations may be isolated or separated from the same sample.

Thus, a preferred embodiment of the invention provides a method of isolating DNA, RNA, and protein from the same sample, said method comprising the following steps:

a) isolating from said sample the populations from which the nucleic acid and protein is to be isolated and preferably isolating one or more specific populations;

b) lysis of the populations, e.g. cell populations, to obtain a sample containing nucleic acid and protein in a free form available for binding to a solid support;

c) contacting sample with an appropriate solid phase under conditions whereby DNA, preferably genomic DNA, becomes bound to the solid support;

d) separation of this solid phase from the remainder of the sample;

e) contacting said remainder of the sample with an appropriate solid phase under conditions whereby RNA, preferably mRNA, becomes bound to the solid support;

f) separation of this solid phase from the remainder of the sample;

g) contacting said remainder of the sample with an appropriate solid phase under conditions whereby a specific protein or population of proteins becomes bound to the solid support;

h) separation of this solid phase from the remainder of the sample.

The method outlined above is a preferred embodiment of the invention and clearly these specific steps can be altered depending on the overall analysis it is wished to achieve to form further embodiments of the invention. In particular, some of the above discussed steps are optional and need not be included. For example, steps a) and b) are optional and whether or not they are carried out depends on the nature of the sample which is initially obtained. If this sample does not contain the nucleic acid and protein which it is desired to analyse in a free and released form, for example if the nucleic acid and protein is contained within cells or tissues or other biological packages, then generally steps a) and b) will be carried out.

In addition, the above described methods describes the sequential isolation of DNA, RNA and protein in separate steps. The isolation of the whole nucleic acid component as one fraction and protein, and the isolation of DNA and protein, and RNA and protein, are also within the scope of the invention and the steps of the method can be adapted as appropriate to fulfil this purpose. For example, if it is desired to isolate the total nucleic acid and protein, step c) can be replaced by a step which involves contacting the sample with an appropriate solid phase under conditions whereby the total nucleic acid component, e.g. DNA and RNA, becomes bound to the solid support. Step e) would then be omitted. If it is desired to isolate DNA and protein then the RNA steps e) and f) can be omitted. Vice versa, if it is desired to isolate RNA and protein then the DNA steps c) and d) can be omitted.

In addition, the nucleic acid and protein isolation steps of the above described-methods can be carried out in any order. Thus, although in a preferred embodiment the order is DNA followed by RNA followed by protein (if all three components are to be analysed), the steps may be carried in any order, e.g. the RNA or the protein may be isolated first. In methods where nucleic acid and protein are to be isolated, or DNA and protein, or RNA and protein are to be isolated, although in preferred embodiments the nucleic acid component is isolated first, the protein component may be isolated first.

In addition, in a further embodiment of the invention the desired nucleic acid and protein components can be isolated simultaneously from the same sample in the same step. This may be achieved in any appropriate manner but will generally be carried out by contacting the sample simultaneously with distinct solid supports which have different surface properties and are able to bind specifically to DNA (e.g. genomic DNA), RNA (e.g. mRNA), all nucleic acid species, or protein, as appropriate. Appropriate solid supports which have specificity for the various nucleic acid and protein components which it is desired to isolate from a particular sample are described herein and any of these may be used. These distinct solid supports with different surface properties may be provided on different areas of the same solid support, or may be provided as separate solid supports which are brought into contact with the sample in the same step. These separate solid supports may conveniently be provided for example as separate dipsticks with different appropriate surface properties. Once the desired nucleic acid and protein components have been isolated in such a single step then they can be used and analysed in the same way as if isolated in separate steps.

Once the desired nucleic acid and protein components have been separated onto solid phases these can be subjected to further analysis, e.g. by conventional methods. Again appropriate methods of further analysis will be discussed in more detail below.

The binding of nucleic acid to a solid support is generally independent of its sequence and the specificity of binding is controlled by varying the properties of the solid support and the conditions under which binding of the nucleic acid is induced. As described above the whole nucleic acid component of a sample can be induced to bind to a solid phase or the appropriate choice of binding conditions and/or nature of the solid support can be effected so that DNA or RNA can be selectively bound to a solid phase, thereby enabling a selective DNA or RNA isolation procedure, which may be carried out simultaneously or preferably sequentially. Appropriate methods and conditions whereby all nucleic acid may be bound or DNA and RNA are selectively bound to a solid phase are well known and documented in the art and any of these methods can be used in the methods of the present invention. Some appropriate and preferred methods are discussed briefly here and in more detail below where alternative methods are also discussed.

Conveniently, where DNA and RNA are isolated in two separate steps the sequential separation may take place using two different solid phases, for example solid supports which can differentiate between DNA and RNA. Thus, such embodiments may comprise carrying out a first separation step to isolate DNA. A further solid support can then be added to the sample to capture the RNA remaining in the sample, either by using a solid support that can bind the RNA, e.g. a silica based support (described in more detail below), or a solid support that can capture specific RNA molecules (e.g. by carrying a complementary nucleic acid probe), or a solid support which can capture a subset of RNA molecules e.g. polyadenylated RNA, using for example a poly-dT or poly-dU based oligonucleotide capture probe. In this way it is possible rapidly to isolate and separate DNA and RNA or subsets of both from the same sample.

In a representative procedure, the sample is lysed in the presence of detergent and the DNA is allowed to bind to a solid support, whereupon the DNA may readily be separated from the sample by removal of the support. Such procedures are described in more detail in WO96/18731 (and in particular Example 12) the disclosure of which is incorporated herein by reference. The procedure of specific DNA capture described in WO96/18731 is also known as the DNA DIRECT method and can be made selective for genomic DNA. Appropriate conditions and methods for carrying out such separations are also described in the Dynabeads DNA DIRECT kit (which is commercially available from Dynal Biotech AS, Oslo, Norway). In methods of the invention where it is desired to isolate DNA and in particular genomic DNA, the DNA DIRECT method of separation is one preferred embodiment. Alternatively, other solid supports having surface chemistries or surface properties supporting DNA binding may be used, for example a support (preferably magnetic beads) carrying surface carboxyl groups.

The RNA may then be isolated from the remaining sample. This can be by a solid phase based system as described above wherein a different solid phase is added to the sample to which RNA becomes specifically bound. Alternatively the same solid phase may be used and the RNA made to bind thereto by inducing an appropriate change in the sample conditions.

Preferably in embodiments where the RNA is isolated by binding to a solid phase, and in the representative procedure as described here, the RNA is mRNA and the surface of the solid phase used has been engineered to carry a capture probe specific for mRNA, e.g. the support has attached to its surface dT oligonucleotides or dU oligonucleotides, e.g. Dynabeads oligo (dT), Dynabeads cDNA release (available from Dynal Biotech ASA) or Dynabeads $T_7$-oligo(dT) (a modified construct) in which a T7 promoter is included following the principles set out in Eberwine et. al., Biotechniques (1996), 20(4): 584-91 and U.S. Pat. No. 5,514,575). The oligonucleotide attached to the "T7 beads" is a combined oligo dT and T7 promoter sequence of the structure 5'AAAAAA-T7sequence (39 nt)-dT(20-25)'. VN is added to the 3'end of the oligonucleotide for Dynabeads $T_7$-oligo(dT).

Appropriate conditions and methods for carrying out such RNA separations are also described in the product inserts provided with the Dynabeads commercial product. In particular Dynabeads oligo (dT) (which are commercially available from Dynal Biotech AS, Oslo, Norway) are sold with an mRNA DIRECT kit protocol which describes how mRNA separation may be carried out. In methods of the invention where it is desired to isolate RNA and in particular mRNA, the mRNA DIRECT method of separation is preferred.

The choice of oligo dT or dU beads to be used depends on the downstream applications of the isolated mRNA (see further discussion below).

Support bound oligo dU may be used for isolation of mRNA as discussed in WO 00/58329 of Dynal Biotech ASA. This is analogous to the use of oligo dT, but with the added advantage that the "U's" provide a site for cleavage by a glycosylase enzyme.

In preferred embodiments, the oligo dT/dU (including the T7 modification) constructs additionally include a further nucleotide sequence (designated "VN", wherein "V" may be any nucleotide other than T (e.g. A, G or C) and "N" may be any nucleotide, including T. This additional "VN" sequence serves the advantageous purpose of assisting in the targeting or positioning of binding of the oligo dU/dT probe sequence to the nucleic acid; the positioning of probe binding is advantageously at the border between the poly A tail and the coding sequence of the mRNA.

In the step of the method where protein is isolated, this is conveniently carried out by any appropriate method using a solid phase with appropriate surface properties. Appropriate methods will depend on the type of proteins it is desired to analyse. In one embodiment specific proteins may be isolated using a solid support, which has an appropriate binding partner/ligand attached to its surface, e.g. an antibody to the particular protein which it is desired to isolate. A particularly preferred antibody to be used in this regard is anti-CK19 (a support, e.g. beads can be coated with anti-CK19 and can be used to isolate specific problems. Anti-CK19 antibodies are commercially available). This thus applies well known principles of affinity separation of proteins, as widely described in the prior art. Any such standard and well known methods may be used or adapted for the present invention.

Alternatively a solid phase with more general surface binding properties can be selected, e.g. a solid phase which has surface chemistry which effects classical chromatography interactions such as ion exchange (including both anion exchange and cation exchange), reverse phase interactions or hydrophobic interactions. Such surfaces are conveniently provided on magnetic beads. The use of these more general surfaces conveniently allows the fractionation of proteins in the sample into subsets depending on the structure and properties (charge, hydrophobicity) etc. of the proteins present.

Such general solid phase surfaces can be prepared using conventional techniques which are standard and well documented in the art of column chromatography. Furthermore, supports (e.g. particles or beads) have been widely described in the art for fluidised bed separation technology, and have properties e.g. ion exchange, designed for protein separation (e.g. U.S. Pat. No. 5,084,169, U.S. Pat. No. 5,079,155 and U.S. Pat. No. 4,732,811). Magnetic particulate solid supports having such surface chemistry are not known in the art and thus form a further embodiment of the invention. A solid support suitable for protein isolation comprises on its surface positively charged amine groups, which are believed to bind negatively charged proteins. The bound proteins may be eluted under conditions of high salt and low pH. Amine beads are available from Dynal Biotech AS as Dynabeads M-270 amine.

In embodiments of the invention where the protein isolation step is carried out after the various nucleic acid isolation steps, the remaining sample may be subjected to any convenient treatment before the protein is isolated using the appropriate solid support. For example, if it is desired to fractionate the proteins present in the sample, for example using the solid supports with more general surface binding properties as described above, this step can be preceded by a step whereby the protein sample is subdivided into different fractions, e.g. subdivided into one or more of membrane fraction, cytosolic fraction and nuclear fraction. Methods for carrying out such subdivision are standard and well documented in the art of protein analysis.

In all the embodiments of the invention described herein, whilst any solid support formats may be used, as well known in the art and widely described in the literature, preferred solid supports are particles and more preferably magnetic particles. Magnetic particles (beads) are well known in the art and widely commercially available. Different sizes of beads are available, or may be prepared, and different applications (e.g. different DNA, mRNA, protein etc. separations) may be optimised on beads of different sizes, e.g. 4.5 µm, 2.8 µm, 2.7 µm, 1.0 µm in diameter.

The methods of the invention are advantageously amenable to automation, particularly if particles, and especially, magnetic particles are used as the support. In a particularly favoured embodiment of the invention, the nucleic acid and protein isolation method is performed using an automated system for handling of the solid support during the cell lysis, nucleic acid binding, protein binding and, optionally, washing steps. Thus the isolated support-bound cells may be transferred to such an apparatus, washed if desired, and lysed; the nucleic acid (i.e. whole nucleic acid component, DNA or RNA) or protein, as appropriate depending on the particular step of the method and the particular support and conditions used may bind to the support, and the bound nucleic acid or protein may readily be washed, using such an apparatus. Furthermore, such an apparatus may also be used to handle the support during the cell/population isolation stage. Thus, it can be seen that the option is there to automate all of the steps of the method if desired.

Particular mention may be made in this regard of the Bead Retriever™, available from Dynal Biotech ASA, Norway. The apparatus has a system for ready and efficient transfer of the support (carrying cells or nucleic acid or protein) from one well to another. Other automated robotic workstations which may be used include the BioMek 2000 with the Dynal MPC-auto96 magnet station and the TECAN GENESIS RSP with its own built in magnet station. Both the BioMek and the TECAN GENESIS RSP are liquid handling robots.

The present invention provides the first description of a technology which can isolate specific cell populations, DNA, mRNA and proteins from the same sample in an automated way, e.g. by carrying out all the steps using a solid phase and in particular a magnetic solid phase. Other methods such as laser microdissection are much slower than the methods described herein, are not automatable and require fixed, sectioned material.

The various reactants and components required to perform the methods of the invention may conveniently be supplied in kit form. Such kits represent a further aspect of the invention.

At its simplest, this aspect of the invention provides a kit for isolating nucleic acid and protein from the same sample comprising:

(a) a solid support suitable for binding nucleic acid components; and (b) a solid support suitable for binding proteins.

In preferred embodiments the supports of (a) comprise supports which are selective for binding to DNA, or supports which are selective for binding to RNA, or both types of support.

Further optional components of the kit include (c) solid supports suitable for isolation of specific cell populations, (d) means for lysing said cells.

The various components (a), (b), (c) and (d) may be as described and discussed above in relation to the methods of the invention.

A further optional component is (e), means for detecting the nucleic acid and/or protein. As discussed above, for detecting nucleic acids such means may include appropriate probe or primer oligonucleotide sequences for use in hybridisation and/or amplification-based detection techniques. For detecting proteins such means include appropriate antibodies.

Optionally further included in such a kit may be buffers, salts, polymers, enzymes etc.

Once one or more nucleic acid and protein components have been isolated onto a solid phase, these can then be analysed or used in any appropriate way. For example, the methods of the invention can be used in any application which involves analysis or comparison of the genome (DNA), transcriptome (RNA) and proteome (expressed protein), or in any analysis where it is desired to compare a particular DNA and/or RNA and the expressed protein, or more preferably a particular DNA, RNA and protein. Such methods are very useful for gene expression studies as they allow analysis and comparison of mRNA levels with protein levels. In addition, the ability to analyse and compare mRNA and protein levels and profiles of samples (e.g. from different cells and tissues) gives a snapshot of the cell's biology. Furthermore, being able to study the mRNA/protein ratio gives an indication of which genes are subject to post-transcriptional regulation. Such ratios are often shifted during disease states, thereby allowing an indication as to which genes may be involved in disease and allowing a study of the possible regulatory mechanisms behind such a shift in mRNA/protein ratio.

The methods of the invention are also useful for example in determining the molecular changes and mechanisms involved in disease states, e.g. determining which genes are mutated, or which proteins are over or under expressed or incorrectly processed. Studying the DNA composition of a sample can provide information on genetic predispositions and acquired mutations, whereas the mRNA and protein profiles generate "molecular portraits" of a cell's biological state or the stage of disease and may also be used for the staging and monitoring of the disease development and treatment. As mentioned above, the methods described are particularly advantageous for such analysis, as they allow the comparison of DNA, RNA and protein from the same sample which is important to allow a more accurate and direct comparison.

The method of the invention also has use as a method for isolating nucleic acid and protein fractions from a single sample.

More specifically, in the case of the DNA, once isolated this can be used in nucleic acid based detection procedures, e.g. in genotyping, SNP analysis, sequencing reactions etc.

Advantageously the bound nucleic acid need not be eluted or removed from the support prior to carrying out the detection step, although this may be performed if desired. Whether or not the nucleic acid is eluted may also depend on the particular method which was used in the nucleic acid binding step. Thus certain nucleic acid-binding procedures will bind the nucleic acid more tightly than others. In the case of DNA-binding using detergents (e.g. by DNA Direct) for example, the nucleic acid will elute from the solid support when an elution buffer or other appropriate medium is introduced. Nucleic acid bound by means of a precipitant such as alcohol or a chaotrope will remain more tightly bound and may not elute when placed in a buffer medium, and may require heating to be eluted. A preferred use of the DNA is in solid phase SNP analysis, which may optionally be fully automated. Such SNP analysis can be carried out using any appropriate technique. For example, PCR can be carried out using one biotinylated primer, followed by single stranded DNA template generation on streptavidin beads, followed by probe annealing, ddN incorporation and a labelling reaction.

Thus, the support-bound nucleic acid may be used directly in a nucleic acid based detection procedure, especially if the support is particulate, simply by resuspending the support in, or adding to the support, a medium appropriate for the detection step. Either the nucleic acid may elute into the medium, or as mentioned above, it is not necessary for it to elute.

A number of different techniques for detecting nucleic acids are known and described in the literature and any of these may be used. Conveniently, nucleic acid may be detected by optical methods, for example by measuring or determining optical density (OD). Alternatively, the nucleic acid may be detected by hybridisation to a probe (which may be a labelled probe for detection) and very many such hybridisation protocols have been described (see e.g. Sambrook et al., 1989, Molecular Cloning: A Laboratory Manual, 2nd Ed. Cold Spring Harbor Press, Cold Spring Harbor, N.Y.). Most commonly, the detection will involve an in situ hybridisation step, and/or an in vitro amplification step using any of the methods described in the literature for this, for example probe annealing/hybridization followed by ddN incorporation (which may be labelled for detection). Thus, techniques such as LAR, 3SR and the Q-beta-replicase system may be used. However, PCR and its various modifications e.g. the use of nested primers, or the use of one or more biotinylated primers will generally be the method of choice (see e.g. Abramson and Myers, 1993, Current Opinion in Biotechnology, 4: 41-47 for a review of nucleic acid amplification technologies).

Other detection methods may be based on a sequencing approach, for example, the minisequencing approach as described by Syvänen and Söderlund, 1990, Genomics, 8: 684-692.

In amplification techniques such as PCR, the heating required in the first step to melt the DNA duplex may release the bound DNA from the support. Thus, in the case of a subsequent detection step, such as PCR, the support bound nucleic acid may be added directly to the reaction mix, and the nucleic acid will elute in the first step of the detection process. The entire isolated support bound nucleic acid sample obtained according to the invention may be used in the detection step, or an aliquot.

The results of the PCR or other detection step may be detected or visualised by many means, which are described in the art. For example the PCR or other amplification products may be run on an electrophoresis gel e.g. an ethidium bromide stained agarose gel using known techniques.

The amplified nucleic acid may also be detected, or the result confirmed, by sequencing, using any of the many different sequencing technologies which are now available, e.g. standard sequencing, solid phase sequencing, cyclic sequencing, automatic sequencing and minisequencing.

If mRNA is isolated, for example using oligo(dT) beads, or oligo(dU) beads (e.g. using Dynabeads oligo(dT), Dynabeads cDNA release or Dynabeads T7 oligo(dT) as described herein) this mRNA can be used or analysed in any appropriate way. The mRNA can for example be analysed using appropriate conventional techniques, e.g. by Northern blotting, or can be used to generate cDNA which may then be subjected to any appropriate DNA based analysis such as those described above.

It can be seen that mRNA and cDNA libraries from specific samples, e.g. specific populations or sub-populations of cells, viruses, etc can be produced using the methods of the invention. This application can either be carried out while the mRNA is still on the solid phase, i.e. resulting in solid phase cDNA libraries, or can be carried out after the mRNA has been eluted. The mRNA may also be used as a substrate for RT-PCR. Solid phase cDNA libraries can be used in any appropriate application and can be re-used, for example as template in different PCRs (or other amplifications), thereby enabling PCR (or other) analysis of multiple transcripts, e.g. from single isolated cells. For example, it can be seen from FIG. 2 that a solid phase c-DNA library has been re-used in multiple PCR experiments to detect different transcripts in cultured carcinoma cells.

If Dynabeads cDNA release beads (or commercial or generic equivalents) are used to isolate the mRNA, as described above, these beads have oligo(dU)VN coupled to their surface. These oligo(dU)VN molecules bind to the mRNA and can be used to prime one strand of solid phase cDNA synthesis. The solid phase cDNA can then be released-enzymatically by UNG treatment and used, e.g. for probe generation for gene expression profiling.

If Dynabeads T7 oligo(dT) beads (or commercial or generic equivalents) are used to isolate the mRNA, as described above, these beads have coupled to their surface a T7 promoter 5-prime to the oligo(dT)VN. After double stranded solid phase cDNA synthesis (first strand synthesis carried out using the oligo (dT) as a primer and second strand synthesis initiated with random hexamers), the T7 promoter (which is a 39 nucleotide sequence specific for the enzyme T7 polymerase, which recognises this sequence in double stranded DNA) can be used to in vitro transcribe antisense RNA and thereby amplify mRNA from small samples for further analysis, or e.g. for probe generation for gene expression profiling, e.g. for microarray analysis. Such probes are conveniently generated by carrying out reverse transcription of the antisense RNA (with random hexamers) to give cDNA which can be labelled and used to probe microarrays. These cDNAs can also be used in a second round of amplification using T7 beads.

Although microarrays are a powerful high throughput tool, they are not very sensitive—at least 1-2 µg of mRNA is required per array. This is often impossible to achieve, e.g. by single cell analysis. Thus, in vitro transcription methods are required to amplify the RNA. For this reason the ability to use the Dynabeads T7 oligo(dT) beads to amplify RNA is advantageous in microarray applications and any other applications where amplification of mRNA is advantageous.

Once isolated by binding to a solid phase using the methods of the invention, subsets of proteins (e.g. those isolated using the supports with more generalised chromatography type surfaces) or individual proteins (e.g. those isolated using supports carrying specific ligands) can be subjected to direct analysis whilst still on the bead (e.g. Bead ELISA) or can be subjected to elution from the solid support followed by analysis by any appropriate conventional technique-such as SDS-PAGE/Western blotting, immunoprecipitation, etc.

As discussed extensively above, one of the main advantages of the method of the invention is that one or more of DNA, RNA and protein can be isolated from the same sample ready for analysis. Thus, results obtained by analysing the DNA, RNA and protein from the same sample using any of the individual techniques described above can be compared as appropriate depending on the aim of the analysis.

If the initial sample contains cells or other biological particles which contain the nucleic acid and protein which is to be analysed, then generally the cells/particles to be analysed will need to be separated from the remainder of the sample. Such separation can be carried out by any of the methods which are standard and conventional in the art, such as sedimentation or centrifugation or cell sorting procedures. Alternatively affinity based separation systems may be used and these are described in more detail below. Such affinity based systems are especially preferred if it is desired to analyse the nucleic acid and protein from a sub-population of the cells or particles contained within the initial sample. Where such affinity-based systems are used, the separation is generally carried out by binding the cells or particles to a solid support carrying an appropriate binding partner.

Affinity-based separation or isolation systems for desired target cells are well known in the art, and rely on the specificity of a binding partner, specific or selective for the target cell, to achieve selective isolation of the cell. Such a system is employed as an optional step according to the present invention in order to achieve selective isolation of one or more particular populations of cells or other biological "particles" from the sample before it is treated in order to free the nucleic acid and protein and provide the nucleic acid and protein containing sample. Thus, a suitable binding partner for use in this regard may be one or more moieties having a binding affinity for the desired cell or other population(s).

The binding partner may be any molecule or moiety capable of binding to the required populations of cells or other particles, but conveniently will be a protein, polypeptide or peptide. Other moieties or molecules of a different chemical nature, for example carbohydrates or small organic molecules may however also be used. Nucleic acid binding partners e.g. aptamers may also be used.

The binding partner may bind to molecules or structures present on the surface of the cells or other particles, for example to cell surface antigens which are expressed (e.g. specifically) on the surface (e.g. cell specific Dynabeads such as Dynabeads Epithelial Enrich, anti CD14, anti CD3, anti CD4, anti CD8, anti CD19). Alternatively, the binding partner may be any moiety binding to a cell surface expressed protein e.g. a cell surface receptor.

The binding partner may, for example, conveniently be an antibody specific for a particular surface antigen. Antibody fragments and derivatives may also be used, according to techniques well known in the art. Methods for preparing such fragments or derivatives are well known in the art and widely described in the literature.

Thus, using knowledge of the molecules or other entities present on the surface of the desired population(s), a binding partner, or combination or mixture of binding partners, may be selected to achieve a desired separation or isolation of cell or other populations from the sample. Advantageously, all or substantially all (i.e. close to all) of the desired cells or other particles present in the sample may be separated. The separation achievable may be dependent not only on the binding partner(s) selected, but also on the nature of the sample, binding conditions etc. Also, biological systems are by their nature variable, and 100% separation may not always be achieved, and, indeed, is not necessary according to the present invention; as in any biological system, some tolerance must be allowed for. However, in preferred embodiments of the invention at least 60%, 65%, 70%, 75%, 80%, 85%, 90% or 95% of the desired populations present in the sample may be separated.

Where more than one different type of binding partner is used they may be attached to the same or different solid supports. Such a system using different solid supports, is applicable particularly in the case of a particulate support such as beads. Thus, different binding partners may be attached to different beads.

In embodiments where more than one different type of binding partner is used, appropriate amounts or ratios at which the different types of binding partner may be used will be readily determined by a person skilled in the art.

As mentioned above, cell separation techniques based on solid phase affinity binding (e.g. immunomagnetic separation (IMS)) are well known in the art and conditions to achieve this may readily be determined by the skilled worker in this field. IMS is a preferred and advantageous cell separation procedure to use, since it enables the isolation of specific cell populations with high purity, for example more than 99% purity from whole blood, as analysed by flow cytometry and molecular techniques. Thus, in the embodiments where a separate affinity isolation step is used, for example a solid support carrying appropriate binding partner(s) may be brought into contact with the sample. A particulate solid support may, for example, be added to the sample contained (e.g. suspended) in an appropriate medium (e.g. a buffer). The support may then be left in contact with the sample (e.g. incubated) for a length of time to enable binding to the cells or other particles to occur. Time/temperature conditions during the step are not critical, and the sample-support mixture may be incubated at e.g. 4 to 20° C. for 10 minutes to 2 hours e.g. 20-45 minutes. As regards other conditions, these may be determined appropriately having regard to the cells under investigation and the isolation methods used, according to principles and procedures known in the art. The cell isolation procedure however focuses on minimizing the probability of affecting the physiological state of the cells and thus enabling downstream molecular characterisation and profiling. Laser capture microdissection can also be used to isolate cell populations for the downstream applications described.

Following cell binding, or any other steps carried out to separate a desired population of cells from which nucleic acid and protein are to be analysed, the isolated or support-bound cells are lysed to release their nucleic acid and protein. Methods of cell lysis are well known in the art and widely described in the literature and any of the known methods may be used. Any of the following methods could, for example, be used: detergent lysis using e.g. SDS, LiDS, Triton-X-100, urea or sarkosyl in appropriate buffers; the use of chaotropes such as Guanidium hydrochloride (GHCl), Guanidium thiocyanate (GTC), sodium iodide (NaI), perchlorate etc; mechanical disruption, such as by a French press, sonication, grinding with glass beads, alumina or in liquid nitrogen; enzymatic lysis, for example using lysozyme, pronases or cellulases or any of the other lysis enzymes commercially available; lysis of cells by bacteriophage or virus infection; freeze drying; osmotic shock; microwave treatment; temperature treatment; e.g. by heating or boiling, or freezing, e.g. in dry ice or liquid nitrogen, and thawing; alkaline lysis. As mentioned above, all such methods are standard lysis techniques and are well known in the art, and any such method or combination of methods may be used. The only requirement is that an appropriate method is chosen such that the species of nucleic acid and protein to be analysed in the subsequent procedure remain substantially intact, i.e. substantially non-degraded.

The use of agents such as solvents, alcohols and chaotropes in isolation methods is sometimes disadvantageous. The present invention affords the advantage that the use of such agents may be avoided. Thus, whilst lysis methods such as those mentioned above using such agents may be employed, in advantageous embodiments of the invention the use of such agents is avoided.

Conveniently, lysis may be achieved according to the present invention by using detergents. An exemplary suitable lysis agent thus includes a detergent such as SDS or another alkali metal alkylsulphate salt, e.g. LiDS, or Sarkosyl or combinations thereof. The lysis agents may be supplied in simple aqueous solution, or they may be included in a buffer solution, to form a so-called "lysis buffer". Any suitable buffer may be used, including for example Tris, Bicine, Tricine and phosphate buffers. Alternatively the lysis agents may be added separately. Salts, for example LiCl and NaCl, may also be included in or added to the lysis buffers. In particular, LiCl is preferred when LiDS is used and NaCl is preferred when SDS is used.

Suitable concentrations and amounts of lysis agents will vary according to the precise system etc. and may be appropriately determined, but concentrations of e.g. 2M to 7M chaotropes such as GTC GHCl, NaI or perchlorate may be used, 0.1M to 1M alkaline agents such as NaOH, and 0.1 to 50% (w/v) e.g. 0.5 to 15% detergent.

To carry out the method of the invention, the support-bound or otherwise isolated cells, may conveniently be removed or separated from the remainder of the sample, thereby concentrating or enriching the cells. To facilitate subsequent steps, it may be desirable, prior to the lysis step, to dilute the isolated cells, e.g. in an appropriate buffer or other medium. If desired the cells may further be treated, e.g. by heating or mixing (e.g. vortexing). A dilution step may be advantageous to prevent agglomeration/aggregation of a particulate support such as beads. Lysis then may conveniently be achieved by adding an appropriate lysis buffer containing the desired lysis agents or by subjecting the isolated cells to the desired lysis conditions. For example, in the case of simply adding a lysis buffer containing appropriate lysis agents, the isolated cells may simply be incubated in the presence of the lysis buffer for a suitable interval to allow lysis to take place. Different incubation conditions may be appropriate for different lysis systems, and are known in the art. For example for a detergent containing lysis buffer, incubation may take place at room temperature or at higher temperatures e.g. 37° C., 50° C. or 65° C. Likewise, time of incubation may be varied from a few minutes e.g. 5 or 10 minutes to hours, e.g. 20 to 40 minutes or 1 to 2 hours. For enzymatic lysis, longer treatment times may be required, e.g. overnight.

Following the obtaining of a sample containing free or released nucleic acid and protein (e.g. following lysis, if required), the steps to be taken will depend on the particular type of analysis it is desired to carry out. For example, in the methods of the invention, solid phases can be used to isolate nucleic acid and protein, DNA and protein, RNA and protein or most preferably DNA, RNA and protein from the same sample. Which entity is isolated depends on the nature of the solid support added and/or the conditions to which the sample and nucleic acid is exposed.

Appropriate conditions and solid supports whereby nucleic acids become bound to the solid support are well known and documented in the art and any of these methods may be used in the embodiments and steps of the invention wherein it is desired that all the released nucleic acids (i.e. DNA and RNA) in a sample are bound to a solid support. Conveniently, the nucleic acid is bound non-specifically to the support i.e. independently of sequence. Thus, for example the released nucleic acid may be precipitated onto the support using any of the known precipitants for nucleic acid, e.g. alcohols, alcohol/salt combinations, polyethylene glycols (PEGs) etc. Precipitation of nucleic acids onto beads in this manner is described for example in WO 91/12079. Thus, salt may be added to the support and released nucleic acid in solution, followed by addition of alcohol which will cause the nucleic acid to precipitate. Alternatively, the salt and alcohol may be added together, or the salt may be omitted. As described above in relation to the cell binding step, any suitable alcohol or salt may be used, and appropriate amounts or concentrations may readily be determined. However, as mentioned above, it is preferred to avoid the use of solvents, alcohols and similar agents. Thus alternative techniques, avoiding the use of such agents are preferred.

In preferred methods of the invention the DNA and RNA are bound to different solid supports in different steps. Again appropriate conditions and solid supports which allow the selective binding of DNA or RNA are well known in the art and any of these techniques can be used. For example, such preferred techniques whereby DNA and RNA can be separated sequentially from the same sample is described in WO96/18731, the teaching of which is incorporated herein by reference.

For example in this regard, by selecting appropriate "nucleic acid binding" conditions (e.g. appropriate buffer or lysis/binding medium compositions), it may be selected whether to bind DNA released from the cells, or RNA released from the cells to the solid support. Thus, "binding medium" compositions may be selected favouring DNA binding (or more particularly genomic DNA binding) to the solid support. Such binding medium compositions include those mentioned above, those described in the Examples below, and the compositions of WO96/18731. For example, a representative DNA binding medium may include GuHCl and optionally EDTA.

Briefly, DNA is bound to appropriate non-specific solid supports in the presence of various detergents as described in WO 96/18731 of Dynal AS (the so-called "DNA Direct" procedure). Various detergent-based systems for binding nucleic acids to a solid support are described in this publication and may be used according to the present invention. The solid support is then separated from the rest of the sample, e.g. by the use of a magnetic field.

To bind RNA, appropriate medium compositions or conditions are known in the art, or may readily be determined from RNA isolation procedures known in the art, and may include, for example, the buffers and procedures described in EP-A-0389063 and U.S. Pat. No. 5,234,809 of Akzo Nobel NV.

Representative RNA-binding compositions may thus include guanidine thiocyanate (GTC) with EDTA.

For RNA binding, the nature of the solid support may be of importance and in particular a "silica" (i.e. comprising silica itself or being based on silica or a silica derivative) solid surface should be used (see further below)

Advantageously, when the method of the invention is used to isolate DNA, it may be combined with a further step separately to isolate the RNA from the sample. Thus, following the procedure discussed above, and selecting DNA-binding conditions in the nucleic acid binding step (e.g. a lysis/binding or binding medium favouring DNA binding), DNA released from the support-bound cells may be bound to the support, and removed from the sample. RNA, most notably mRNA, released from the leucocytes, remains in the sample (more precisely in the supernatant). This RNA may readily be isolated from the sample using standard procedures, for example by binding to a capture probe, conveniently immobilised (e.g. by binding to a solid support), consisting of oligo dT.

A further solid support can then be added to the sample under conditions such that the RNA in the sample becomes captured. This can be done by for example suing a solid support that can bind the RNA or a solid support that can capture specific RNA molecules (e.g. by carrying a complementary nucleic acid probe), or a subset if RNA molecules, e.g. by carrying a capture probe for polyadenylated RNA, i.e. specific for mRNA.

Conveniently, the nucleic acid or DNA binding step may take place simultaneously or concomitantly with the cell lysis step. This may conveniently be achieved using the detergent-based methods of WO96/18731. Thus, for example, an agent or agents for lysis and nucleic acid binding may conveniently be contained in an appropriate medium (e.g. a buffer or other aqueous solution) and added to the support-bound cells. The cells may then be maintained in contact with the medium e.g. incubated (e.g. as described above) to allow lysis and nucleic acid binding to take place. Such a medium may be referred to as a "lysis/binding" medium. A detergent may function as both lysis agent and to assist in the binding of the nucleic acid to the support.

The detergent may be any detergent, and a vast range are known and described in the literature. Thus, the detergent may be ionic, including anionic and cationic, non-ionic or zwitterionic. The term "ionic detergent" as used herein includes any detergent which is partly or wholly in ionic form when dissolved in water. Anionic detergents have been shown to work particularly well and are preferred. Suitable anionic detergents include for example sodium dodecyl sulphate (SDS) or other alkali metal alkylsulphate salts or similar detergents, sarkosyl, or combinations thereof.

Conveniently, the detergent may be used in a concentration of 0.2 to 30% (w/v), e.g. 0.5 to 30%, preferably 0.5 to 15%, more preferably 1 to 10%. For anionic detergents concentrations of 1.0 to 5% e.g. 0.5 to 5% have been shown to work well.

The detergent may be supplied in simple aqueous solution, which may be alkaline or acidic, or more preferably in a buffer. Any suitable buffer may be used, including for example Tris, Bicine, Tricine, and phosphate buffers. Conveniently, a source of monovalent cations, e.g. a salt, may be included to enhance nucleic acid capture, although this is not necessary. Suitable salts include chloride salts, e.g. sodium chloride, lithium chloride etc. at concentrations of 0.1 to 1M, e.g. 250 to 500 mM. As mentioned above, other components such as enzymes, may also be included.

Other optional components in the detergent composition include chelating agents e.g. EDTA, EGTA and other polyamino carboxylic acids conveniently at concentrations of 1 to 50 mM etc., reducing agents such as dithiothreitol (DTT) or β-mercaptoethanol, at concentrations of for example 1 to 10 mM.

Preferred detergent compositions may for example comprise:

100 mM Tris-HCl pH 7.5
10 mM EDTA
2% SDS
or:
100 mM TrisCl pH 7.5
10 mM EDTA
5% SDS
10 mM NaCl
or:
100 mM TrisCl pH 7.5
500 mM LiCl
10 mM EDTA
1% LiDS Reference is made to WO96/18731 for further details, exemplary reaction conditions etc.

Alternative nucleic acid binding techniques may also be used in order to achieve the step of binding released nucleic acid to the solid support. For example, one such method may take advantage of the well known principle of nucleic acid binding to a silica surface.

Thus, in such an embodiment, the solid support may comprise or consist of a silica or silica-based or derived material. Many such materials are known and described in the art, and the literature is replete with references describing the isolation of nucleic acids by binding to silica surfaces (see e.g. EP-A-0389063 of AKZO N.V., U.S. Pat. No. 5,342,931, U.S. Pat. No. 5,503,816 and U.S. Pat. No. 5,625,054 of Becton Dickinson, U.S. Pat. No. 5,155,018 of Hahnemann University, U.S. Pat. No. 6,027,945 of Promega Corp. and U.S. Pat. No. 5,945,525 of Toyo Boseki KK).

Ionic binding of the nucleic acid to the support may be achieved by using a solid support having a charged surface, for example a support coated with polyamines.

The support which is used in the method of the invention may also carry functional groups which assist in the specific or non-specific binding of nucleic acids, for example DNA binding proteins e.g. leucine zippers or histones or intercalating dyes (e.g. ethidium bromide or Hoechst 42945) which may be coated onto the support.

Likewise, the support may be provided with binding partners to assist in the selective capture of nucleic acids. For example, complementary DNA or RNA sequences, or DNA binding proteins may be used. The attachment of such proteins to the solid support may be achieved using techniques well known in the art. Conveniently, such nucleic acid-binding partners may be intermixed on the solid support with the anti-leucocyte binding partners.

The solid supports used for any of the steps of the methods described herein may be any of the well known supports or matrices which are currently widely used or proposed for immobilisation, separation etc. These may take the form of particles, sheets, gels, filters, membranes (e.g. nylon membranes), fibres, capillaries, needles or microtitre strips, tubes, plates or wells, etc, combs, pipette tips, micro arrays, chips, or indeed any solid surface material.

Conveniently the support may be made of glass, silica, latex, plastic or any polymeric material. Generally speaking, for isolation of nucleic acids, the nature of the support is not critical and a variety of surface materials may be used. The surface of the solid support may be hydrophobic or hydrophilic. Preferred are materials presenting a high surface area for binding of the cells, and subsequently, of the nucleic acid. Such supports will generally have an irregular surface and may be for example be porous or particulate e.g. particles, fibres, webs, sinters or sieves. Particulate materials e.g. beads are generally preferred due to their greater binding capacity, particularly polymeric beads/particles.

Conveniently, a particulate solid support used according to the invention will comprise spherical beads. The size of the beads is not critical, but they may for example be of the order of diameter of at least 1 and preferably at least 2 µm, and have a maximum diameter of preferably not more than 10 and more preferably not more than 6 µm. For example, beads of diameter 2.8 µm, 2.7 µm and 4.5 µm have been shown to work well.

Monodisperse particles, that is those which are substantially uniform in size (e.g. size having a diameter standard deviation of less than 5%) have the advantage that they provide very uniform reproducibility of reaction. Monodisperse polymer particles produced by the technique described in U.S. Pat. No. 4,336,173 are especially suitable.

Non-magnetic polymer beads suitable for use in the method of the invention are available from Dynal Biotech AS as well as from Qiagen, Amersham Pharmacia Biotech, Serotec, Seradyne, Merck, Nippon Paint, Chemagen, Promega, Prolabo, Polysciences, Agowa, Bangs Laboratories and Dyno Particles or Dyno Specialty Polymers.

However, to aid manipulation and separation, magnetic beads are preferred. The term "magnetic" as used herein means that the support is capable of having a magnetic moment imparted to it when placed in a magnetic field, and thus is displaceable under the action of that field. In other words, a support comprising magnetic particles may readily be removed by magnetic aggregation, which provides a quick, simple and efficient way of separating the particles following any cell, nucleic acid and protein binding steps, and is a far less rigorous method than traditional techniques such as centrifugation which generate shear forces which may disrupt cells or degrade proteins or nucleic acids.

Thus, using the method of the invention, the magnetic particles with cells, nucleic acids, or proteins attached may be removed onto a suitable surface by application of a magnetic field e.g. using a permanent magnet. It is usually sufficient to apply a magnet to the side of the vessel containing the sample mixture to aggregate the particles to the wall of the vessel and to remove the remainder of the sample for further steps.

Especially preferred are superparamagnetic particles for example those described by Sintef in EP-A-106873, as magnetic aggregation and clumping of the particles during reaction can be avoided, thus ensuring uniform cell, nucleic acid and protein extraction. The well-known magnetic particles sold by Dynal Biotech ASA (Oslo, Norway, previously Dynal AS) as DYNABEADS, are particularly suited to use in the present invention. Beads are also automation friendly and allow binding at varying salt concentrations and/or pH. Beads also allow the possibility to manipulate binding and elution conditions of single samples.

Functionalised coated particles for use in the present invention may be prepared by modification of the beads according to U.S. Pat. Nos. 4,336,173, 4,459,378 and 4,654,267. Thus, beads, or other supports, may be prepared having different types of functionalised surface, for example positively or negatively charged, hydrophilic or hydrophobic.

In embodiments where an affinity-based separation of cells or other particles is used, the binding partner(s) may be attached to the solid support in any convenient way, before or after binding to the cells/particles, according to techniques well known in the art and described in the literature. Thus the binding partner may be attached directly or indirectly to the solid support.

In a convenient embodiment, the binding partner may be attached to the support, prior to contact with the sample. Such attachment may readily be achieved by methods (e.g. coupling chemistries) well known in the art, and conveniently the binding partner is bound directly to the solid support, for example by coating. However it may also be attached via spacer or linker moieties. The binding partner may be covalently or reversibly attached according to choice.

Alternatively, as mentioned above, the binding partner may first be brought into contact with the sample, to bind to the cells/particles before being attached to the solid support. In this case, the solid support may conveniently carry or be provided with a binding moiety capable of binding to the particular specific binding partner used. Again, such binding systems are well known in the art. For example, the solid surface may carry a (secondary) antibody capable of binding to the particular binding partner (e.g. a polyclonal anti-species antibody).

In an advantageous embodiment of the invention the lysis step of the method (and indeed the other steps of the method involving the use of a solid support) may include a further step involving the addition of a further or extra amount of solid support (also referred to herein as a "second" solid support) to the reaction mixture.

The use of a second solid support has been found to offer advantages in sample collection for example by improving pellet formation and hence isolation of the first solid support. The improved pellet formation may also reduce non-specific binding of substances or entities in the pellet, or in other words reduces contamination of the pellet. Whilst not wishing to be bound by theory it is believed that when only a first solid support is used the isolated nucleic acid binds to the first solid support as a loose, non-compact mesh, thereby resulting in a relatively loose non-compact pellet. However, where a second support is used and particularly when this second solid support comprises particles which are smaller or larger than the first solid support, the second solid support fills in the gaps (or vice versa) in the loose mesh, thereby making the pellet tighter and more compact thus reducing the tendency to trap contaminating material.

Further details of the nature and characteristics of appropriate second solid supports for use in the methods of the present invention are described in WO 01/94572, the disclosure of which is incorporated herein by reference.

Briefly, the second solid support may be of comparable size and density to the first solid support. Preferably however, the second solid support is of a smaller size than the first solid support. For example, where the supports are particulate the second solid support comprises particles of a smaller diameter (e.g. approximately half the diameter), than those comprising the first solid support. In especially preferred embodiments the first solid support comprises particles of 4.5 µm diameter (e.g. the M450 beads described herein) whereas the second solid support comprises particles of 2.8 µm diameter (e.g. the M280 and M270 beads described herein). Alternatively, the first support may be smaller than the second support and the dimensions described above may be reversed.

Especially preferably the second solid support may take a more active role in the isolation of the nucleic acid and in such cases the second solid phase is capable of binding to nucleic acid, i.e. has nucleic acid binding properties. Preferably therefore the second solid support may be made of glass, silica, latex, plastic or any polymeric material (i.e. an uncoated surface) capable of binding nucleic acid and such a solid support may optionally be functionalised, for example to aid or improve nucleic acid binding. Particularly preferred in this regard are functionalised solid supports which have a surface charge, preferably a negative surface charge. Most preferred are solid supports coated with carboxylic acid functional groups. Such solid supports are commercially available, for example the M-270 carboxylic acid beads or M-280 Hydroxyl beads manufactured by Dynal Biotech ASA. Preferably the second solid supports are particulate, e.g. beads, and especially preferably are magnetic.

The provision of a further or extra amount of solid support after the cell isolation step results in an improved yield of nucleic acid and also makes the elution of nucleic acid from the solid support easier, particularly where solid supports with a negatively charged surface are used. Whilst not wishing to be bound by theory, as described above it is believed that the addition of an extra amount of a "second" solid support improves the compactness of the bead and nucleic acid pellet and particularly where DNA is able to bind to the second solid support, more effective and complete binding of nucleic acid molecules, rather than the nucleic acid molecules being attached to the beads only at one end or being attached to the beads loosely is achieved.

The terms "additional" or "extra" or "further" amount when used herein in connection with the addition of a second solid phase, is used to indicate the addition of any amount (by weight) of second solid phase such that the isolation of nucleic acid is improved, for example the yield of isolated nucleic acid is improved. For example the amount of second solid phase added might be the same amount as the amount of first solid phase used or may be up to approximately 3 to 5 times the amount of first solid phase used. Alternatively, the amount of second solid phase added may be less than the amount of first solid phase providing that the isolation of nucleic acid is improved. Preferably the amount of second solid support used is 0.5 to 3 times the amount of first solid phase.

As the "amount" of solid phase refers to the weight of the solid phase, in the preferred embodiments of the invention where the first and second solid phases are particulate and the particles making up the second solid phase are smaller (or larger) than the particles making up the first solid phase, the number of particles used for the first and second solid phases will generally be different.

BRIEF DESCRIPTION OF DRAWINGS

The invention will now be described in more detail in the following non-limiting Example, with reference to the drawings in which:

FIG. 1b represents a schematic diagram showing a summary of a model system according to the present invention; carcinoma cells (SW480) that have been spiked into blood sample, are isolated by positive selection, binding to beads carrying anti-Ber EP4 (Dynabeads Epithelial enrich). DNA is isolated from the captured carcinoma cells by lysing the cells and adding DNA binding Dynabeads, from which it may be eluted in purified form, e.g. for subsequent analysis. Different blood cell population (e.g. B-cells, T-cells, monocytes) may be isolated from the remaining blood sample subsequently, and subjected to DNA isolation as described. The isolated cell populations may be subjected to mRNA and protein isolation.

FIG. 4A shows the results of Bead-DELFIA following specific protein isolation using anti-CK19; FIG. 4B shows the results of SDS-PAGE comparing the cell lysate against a fractionated cell lysate (fractionated by binding to Dynabeads® M270-amine).

FIG. 5a shows the results of an IMS separation of B cells by CD19-IMS and T cells by CD3-IMS, CD8-IMS and CD4-IMS, where mRNA from each cell population isolated after gDNA removal is subjected to an RT-PCR for CD19 as described in Example 2. The gels compare the amount of CD19 (and hence B cells) present in each sample to investigate unspecific binding in IMS;

EXAMPLE 1

Combined Isolation of Nucleic Acid and Proteins from Single Samples

Figure 3:
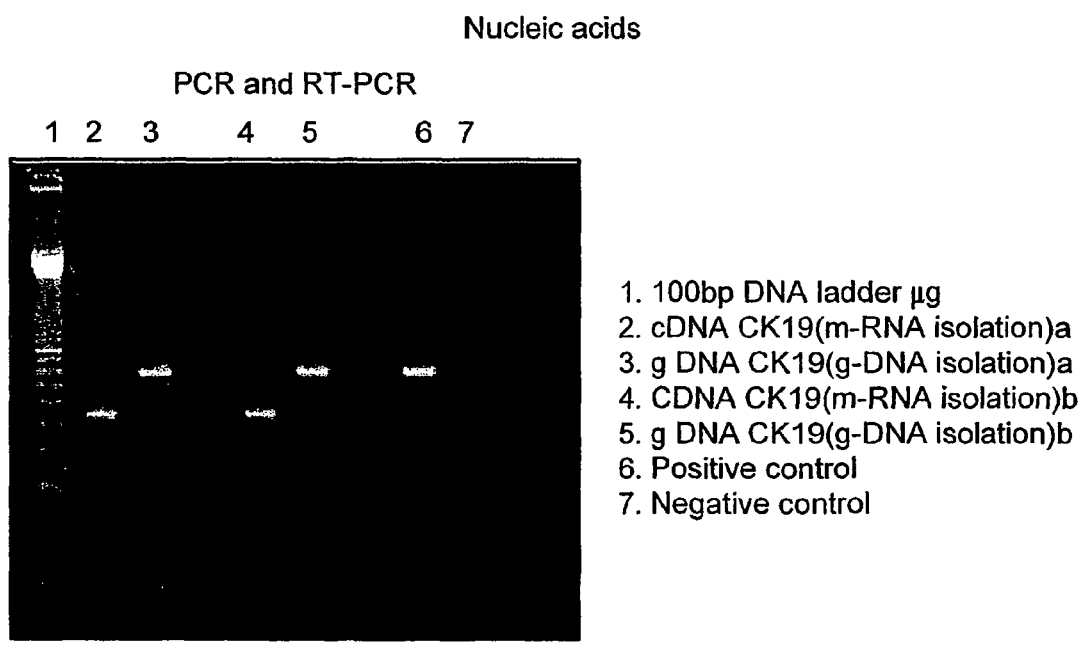
FIG. 3 is a photograph of a gel showing the results of PCR and RT-PCR experiments carried out as described in Example 1, showing isolation of genomic DNA (gDNA) and mRNA encoding CK19 sequentially from the same sample: Lane 1—100 bp DNA ladder 1 µg; Lane 2—cDNA CK19 (mRNA isolation)a; Lane 3—gDNA CK19 (g-DNA isolation)a; Lane 4—cDNA CK19 (mRNA isolation)b; Lane 5—gDNA CK19 (gDNA isolation)b; Lane 6—Positive control; Lane 7—Negative control.

Experimental Procedures:

Cell pellets containing $2\times10^5$ cultured carcinoma cells (SW480) were lysed in 200 μl lysis-binding buffer (100 mM Tris-HCl pH 7.5, 500 mM LiCl, 10 mM EDTA pH 8.0, 5 mM DTT, 1% LiDS) containing Dynabeads Epithelial. Enrich (200 μg) which were present to improve pellet formation and Dynabeads M270 carboxylic Acid (300 μg), which bind the DNA. DNA is isolated by incubating the mix on a roller at room temperature for 5 minutes. The bead-DNA complex is separated from the remaining lysate, and washed 3×500 μl in 1× washing buffer (10 mM Tris-HCl pH 7.5, 150 mM LiCl, 1.0 mM EDTA), followed by elution in 100 μl elution buffer (10 mM Tris-HCl pH 8.0, 0.01% Tween 20) at 80° C. for 5-10 minutes. The DNA is ready for e.g. PCR (1 μl is more than enough). Reference is made to FIG. 3 which shows gel analysis of PCR products obtained from inter alia, isolated genomic DNA.

Figure 1A:
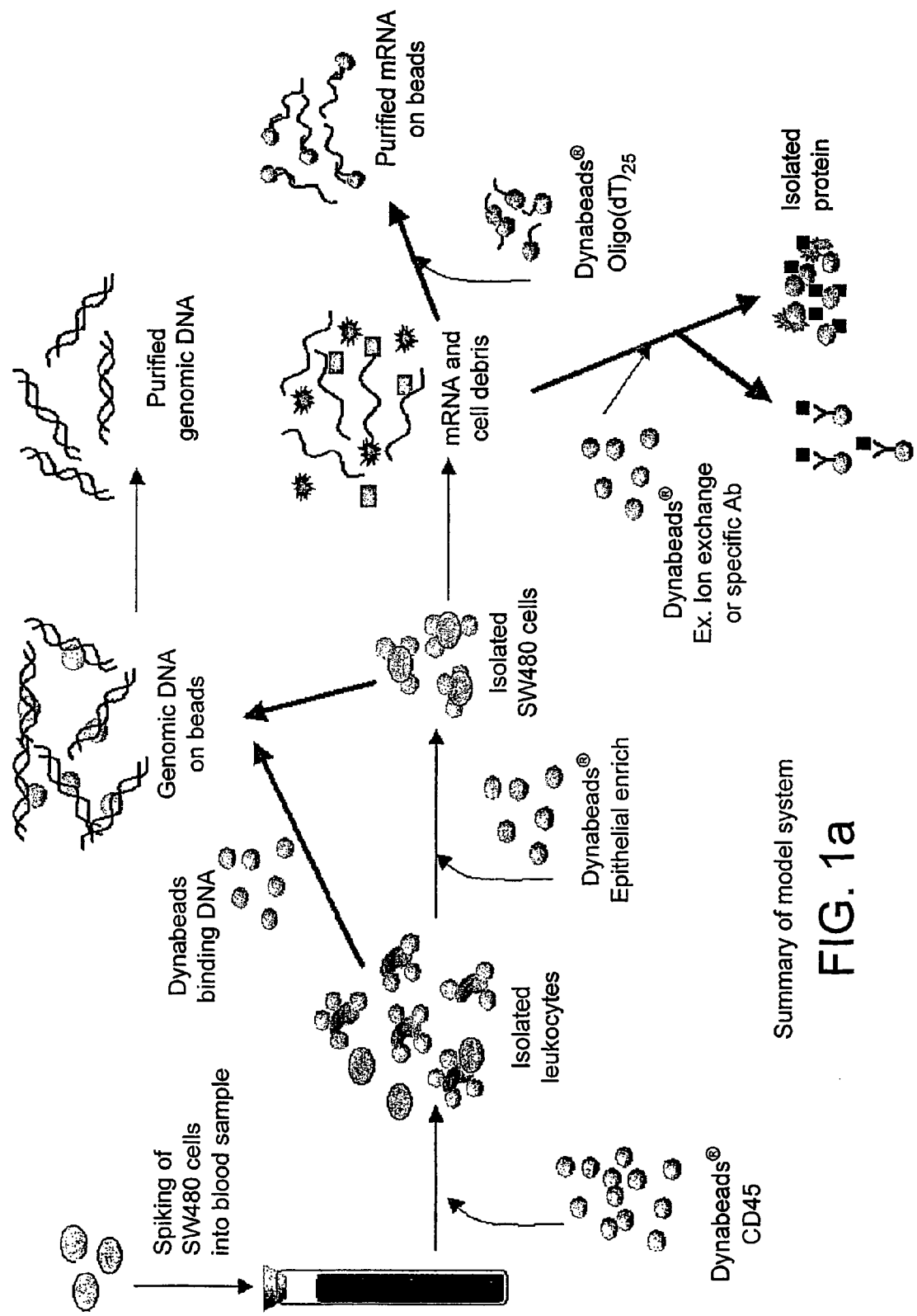
FIG. 1a represents a schematic diagram showing a summary of a model system according to the present invention; leukocytes are isolated by positive selection, binding to beads carrying anti-CD45. DNA is isolated from the captured leukocytes and bound onto DNA-binding beads, from which it may be eluted in purified form, e.g. for subsequent analysis. As an alternative, the isolated leukocyte population may be further fractionated by selection for circulating carcinoma cells (SW480 cells; Ber EP4$^+$ cells) using beads (Dynabeads® Epithelial Enrich) carrying a specific binding partner for such cells. This fractionated population may also be subjected to genomic DNA isolation as previously, allowing the general (e.g. leukocyte) and sub-fractionated (e.g. SW$_4$80) cell populations to be compared. The isolated cell populations may be subjected to mRNA and protein (specific or general fraction) isolation.
Figure 2:
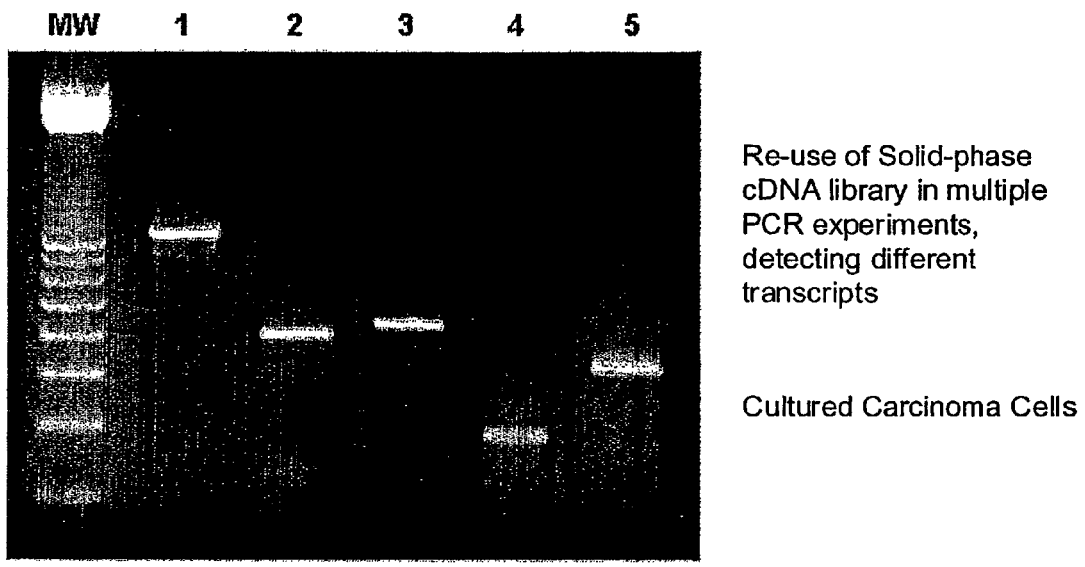
FIG. 2 is a photograph of a gel showing the results of sequential PCR experiments carried out as described in Example 1 on solid phase cDNA obtained from isolated mRNA (isolated from cultured carcinoma cells spiked into blood samples), in order to detect different transcripts: Lane 1—ESX (1st round of PCR); lane 2—Mucin 1; Lane 3—CK19 (third round of PCR); Lane 4—CK19 (first (nested) round of PCR); Lane 4—ESX (second (nested) round of PCR)

To the remaining lysate, 20 μl oligo(dT) beads (Dynabeads® Oligo (dT) 25 can be used) were added and mRNA annealed for 5 minutes at room temperature on roller. Bead-mRNA complex is separated from the remaining lysate, washed (as standard Dynal procedure ie. as indicated by the manufacturer) and resuspended in 100 μl ice cold 10 mM Tris-HCl, and ready for RT-PCR. The results are shown in FIGS. 2 and 3.

Figure 4:
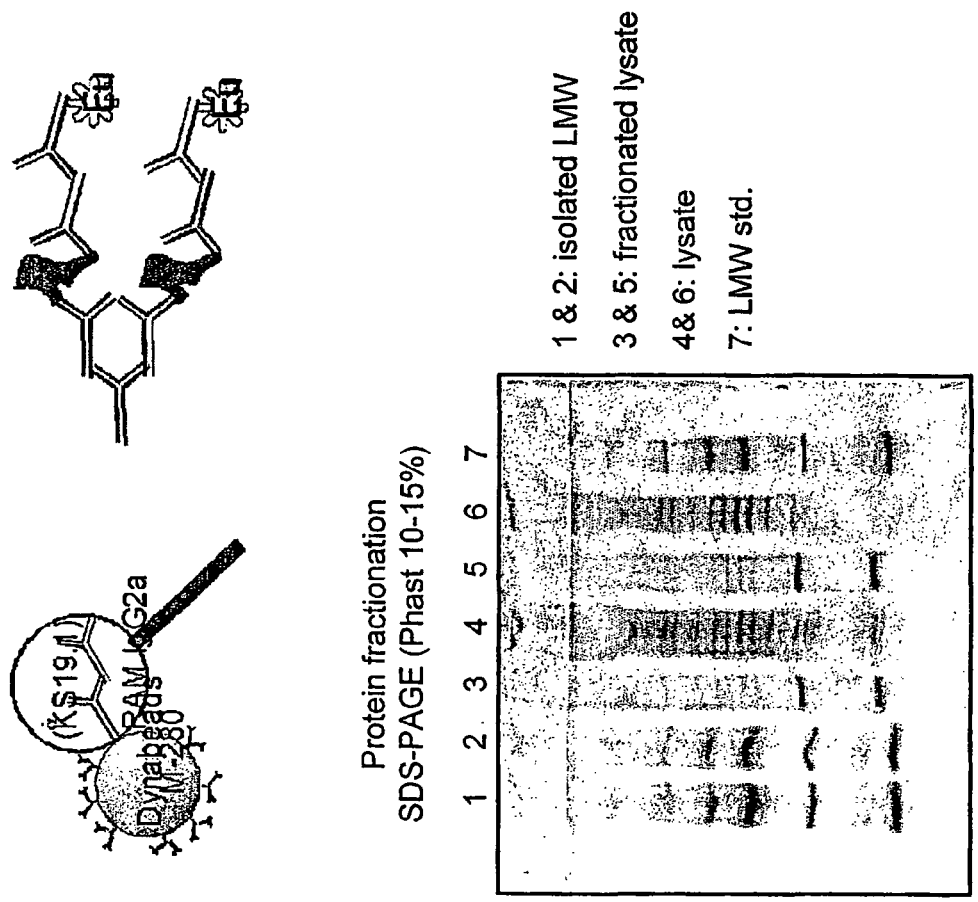
FIG. 4 shows the results of protein fractionation of a cultured carcinoma cell sample as described in Example 1.
Figure 4:
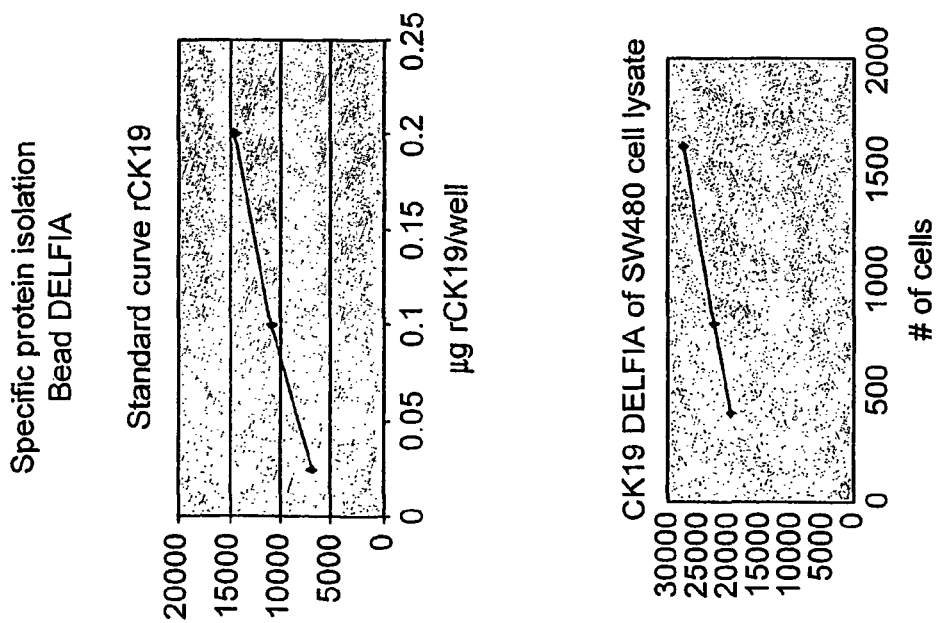

The remaining lysate is diluted (200 μl lysate+800 μl 10 mM Tris-HCl pH 8.0) and added to 1.5 mg Dynabeads M270-amine, which have been pre-washed in 10 mM Tris-HCl pH 8.0. The suspension is incubated on a roller for 1 hour at room temperature. The bead-protein complex is then washed 3×100 μl in 10 mM Tris-HCl pH 8.0, and eluted by boiling all the beads for 2-5 minutes in 10 μl SDS-PAGE sample buffer (20 mM Tris-HCl pH 8.0, 1 mM EDTA, 2.5% SDS, 5% b-mercapto-ethanol, 0.01% BPB) and 1 μl is applied on 10-15% SDS-PAGE Phast gel. The results are shown in FIG. 4 (specifically in FIG. 4B).

For specific protein isolation, the lysate was diluted: 5 μl, 10 μl and 20 μl lysate in 100 μl PBS with 0.1% BSA, prior to bead-DELFIA (ie separation of specific CK19 protein using anti-CK19 beads). The results are shown in FIG. 4A.

Isolated LMW in FIG. 4B refers to experiments where we dissolved Low Molecular Weight standard (MW protein from Amersham Pharmacia) in lysis/Binding buffer to a conc. of 1 μg/μl and mixed 20 μl of this with 80 μl 10 mM Tris-HCl, added 1.5 mg amine beads and incubated and washed, eluted and analysed as described for lysate. This shows that the beads bind proteins.

EXAMPLE 2

Isolation of Cell Populations by IMS (Immunomagnetic Separation)

The presence/co-isolation of B cells in different populations of T cells isolated by IMS were investigated. Cells positive for CD19, CD3, CD8 and CD4 were selected by IMS, gDNA was removed and mRNA was then extracted from the isolated cell populations and cDNA was synthesised. PCR was then carried out using CD19 primers on a dilution series for each sample, representing from 40 000 to 75 cells. The results for this experiment can be seen in FIG. 5a, where the sensitivity of the CD19 RT-PCR is indicated in the first gel panel. The remaining gels demonstrate the low level of unspecific binding in IMS, since CD19 PCR for the T cell populations demonstrated weak bands and hence only a very low level of unspecific B cell binding had occurred.

Figure 5B:
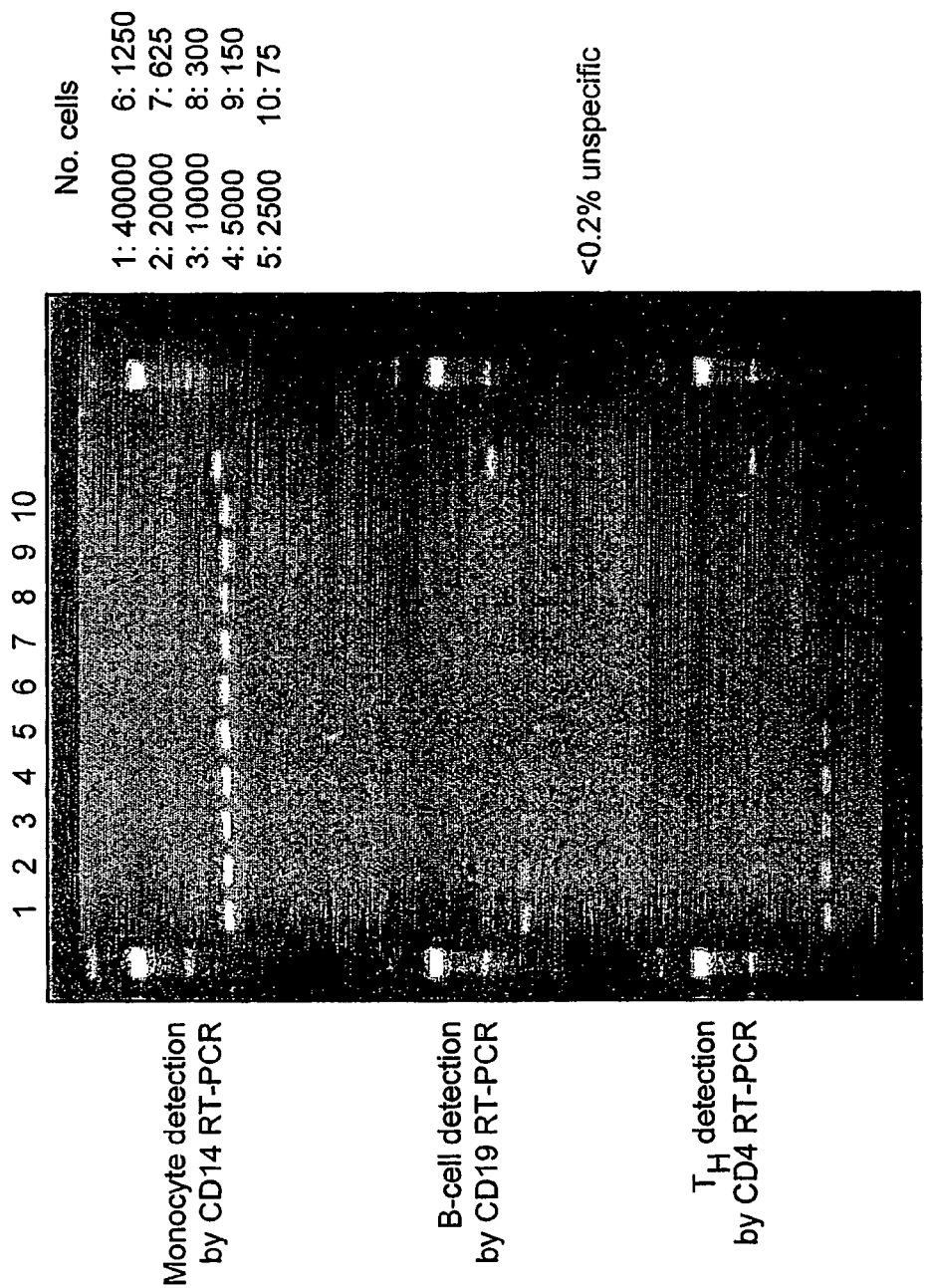
FIG. 5b shows the results of an IMS separation of monocytes by Dynabeads CD14, as described in Example 2. This figure shows that RT PCR for CD14 gives a positive result, but RT PCR for CD19 or CD4 result in only low levels being detected and hence demonstrates the low levels of unspecific binding for IMS.

A similar experiment was carried out, demonstrating a low level of unspecific B cell binding or TH cell (T helper cells) binding (<0.2% unspecific) when IMS was used with CD14 to isolate monocytes (FIG. 5b).

EXAMPLE 3

Spiking of Carcinoma Cells into a Blood Sample and the Isolation of the Carcinoma Cells by IMS Cultured colon carcinoma cells (SW480) were resuspended in culture medium, diluted and counted in a Coulter counter. Different numbers of carcinoma cells (from $1\times10^6$ to 1 cell) were spiked into diluted blood samples (1 ml whole blood+1 ml DPBS) or used directly as positive controls. Unspiked blood samples were treated identically and served as negative controls. Samples were kept at 4° C.

Pre-washed Dynabeads Epithelial Enrich ($4\times10^7$ beads) were added to each spiked and un-spiked blood sample, and the samples were incubated at 4° C. for 15 minutes on a roller.

The cell-bead complex was captured by applying a magnet, washed once in cold DPBS/0.1% BSA and transferred to a new tube. The cell-bead complex was washed 3 times in 1 ml cold DPBS. In the last wash, the sample was split by transferring 500 µl resuspended bead-cell complex to a new tube (sample a/b).

Sample a ($5 \times 10^5$ Cells):

DNA Isolation

Washing buffer was removed, and the rosetted cells were lysed by adding lysis-binding buffer, containing DNA binding Dynabeads. The cell lysate was incubated at room temperature, on a roller for 5 minutes.

Figure 8:
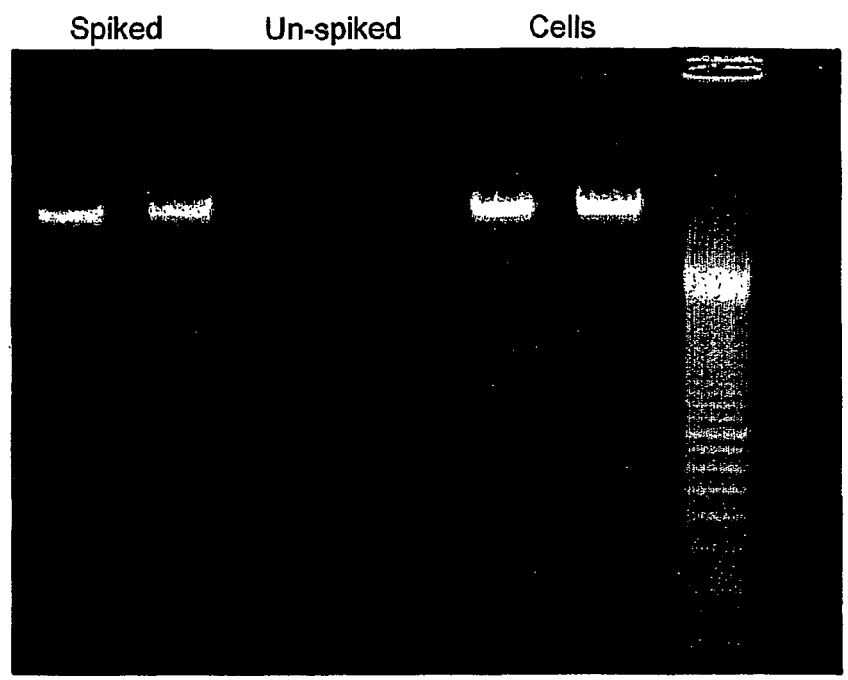
FIG. 8 shows that DNA obtained from IMS isolated cells is not degraded.

The DNA-bead complex was captured by applying a magnet. The supernatant, containing mRNA and proteins was transferred to a new tube. The DNA-bead complex was washed 3× in 1× washing buffer (10 mM Tris-HCl pH 7.5, 150 mM LiCl, 1.0 mM EDTA) by turning the tube upside down 3-5 times. After the third wash, the DNA-bead complex was resuspended in Elution buffer (10 mM Tris-HCl pH 8.0, 0.01% Tween 20) and the tube incubated at 80° C. for 10 minutes. The eluted DNA was transferred to a new tube and was ready for e.g. PCR (1 µl is more than enough). As can be seen from FIG. 8, there was no degradation of the DNA.

Subsequent mRNA Isolation

The remaining lysate was subjected to mRNA isolation by adding pre-washed Dynabeads oligo(dT)25 and incubated at room temperature on a roller for 5 minutes.

The mRNA-bead complex was captured by applying a magnet and washed 2× in washing buffer with LiDS, 2× in washing buffer without LiDS and 1× in 10 mM Tris HCl pH 7.5 (as standard Dynal Procedure . . . ) and was then ready for cDNA synthesis or RT-PCR. cDNA synthesis was performed as follows:

Solid-phase cDNA was synthesised by using the oligo (dT)-sequences on the beads as primer in 1st strand cDNA synthesis. cDNA was synthesised using Thermoscript, following the manufacturers protocol except for the incubation step. Samples were incubated for 30 minutes at 50° C. followed by 30 minutes at 65° C. with constant mixing. The solid-phase cDNA was used as template in PCR.

Figure 6:
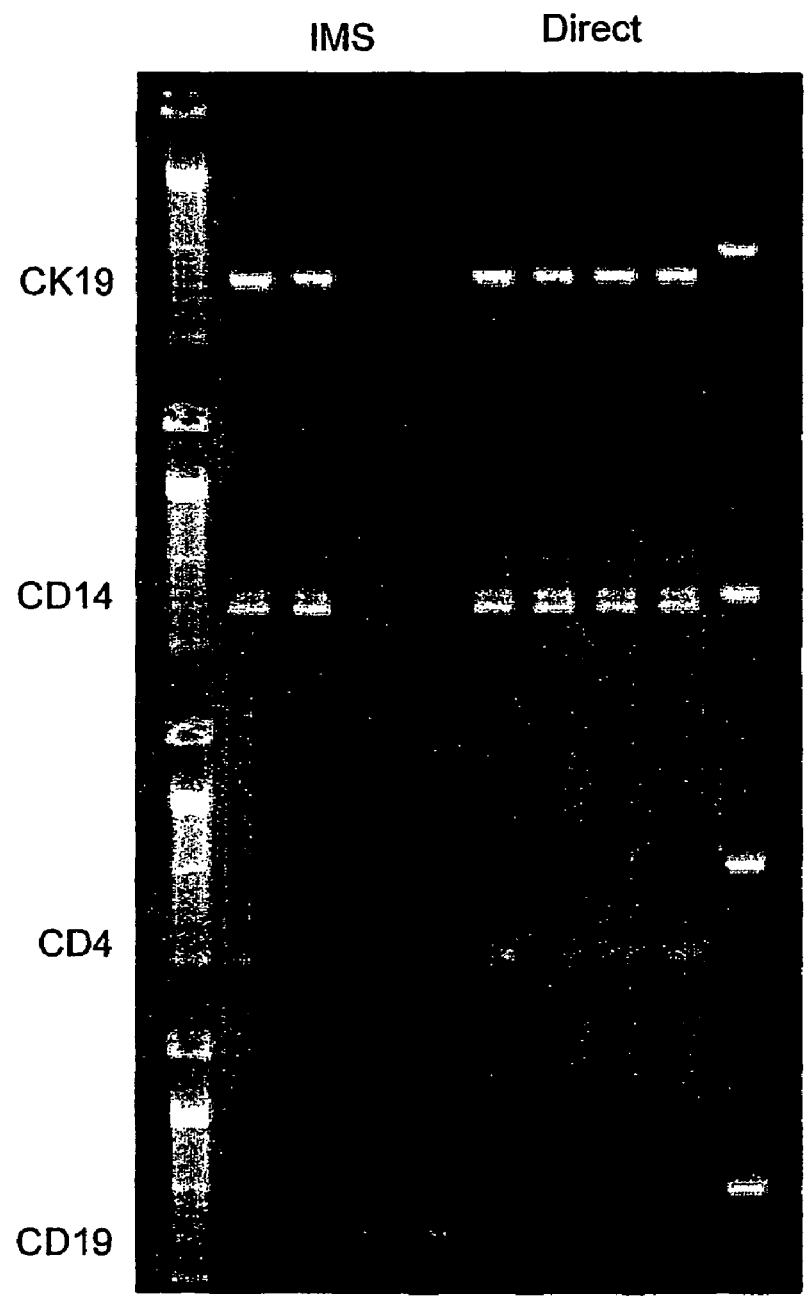
FIG. 6 shows the results of an IMS separation of carcinoma cells from whole blood (into which they had been spiked), where RT PCR for CK19 gives a positive result indicating the isolation of the carcinoma cells. RT PCRs for CD4 and CD14 are not detected and CD19 barely detected in the negative controls (unspiked blood samples, lanes 3 and 4) and this again demonstrates that only low levels of unspecific binding occur for IMS.
Figure 7:
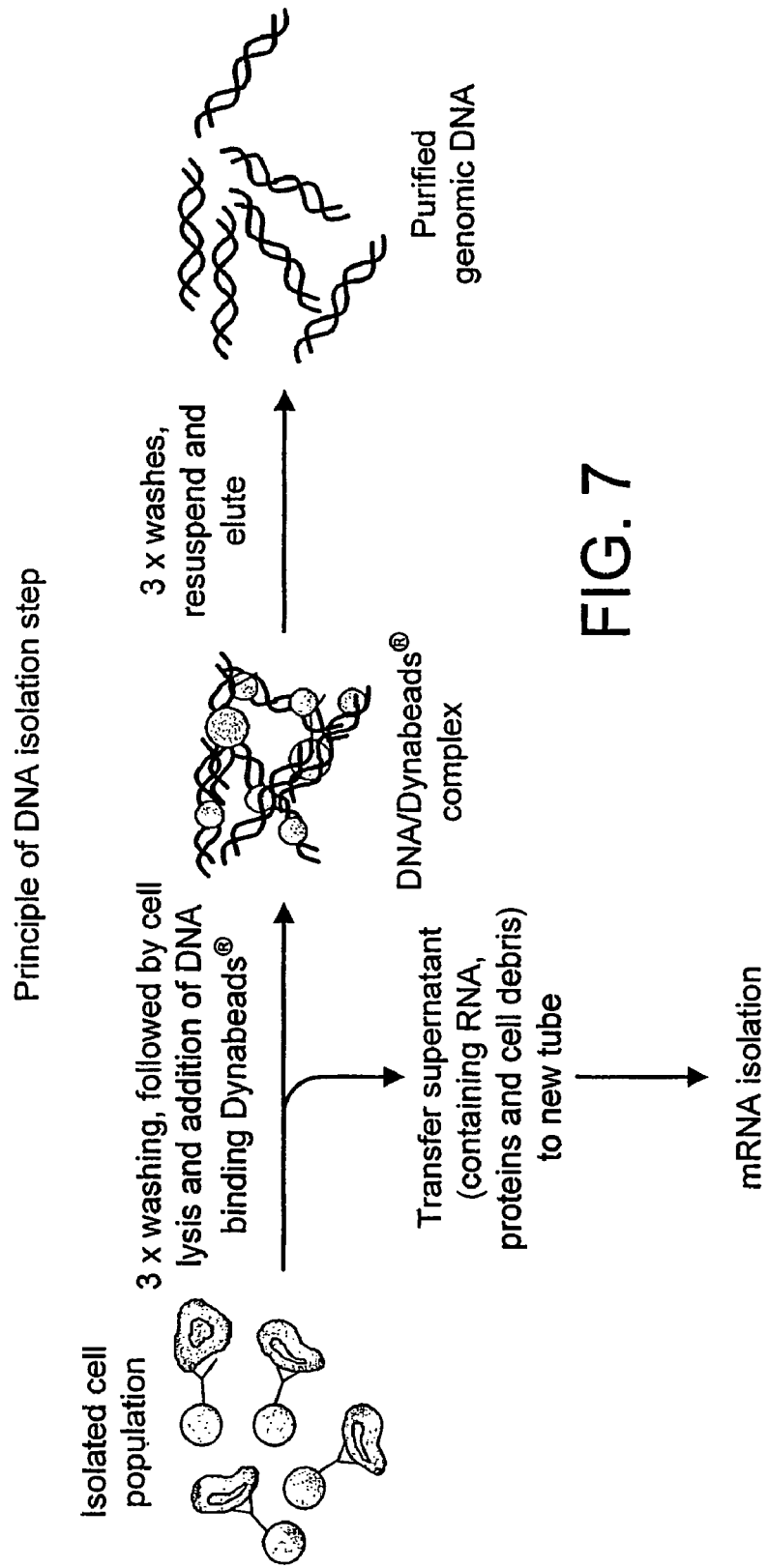
FIG. 7 is a schematic representation of the DNA isolation protocol in Example 3.

PCR was then carried out using CK19 primers, which amplify a transcript not present in blood. The isolation of carcinoma cells could be seen from the results of the CK19 PCR. CD14, CD4 and CD19 PCRs were then carried out to show the specificity of the IMS process for isolating carcinoma cells in this experiment rather than blood cells (FIG. 6a).

EXAMPLE 4

Protein Isolation with Anion and Cation Exchanger Beads

Protein fractionation from carcinoma cells was carried out using 50 µl (1.5 mg) ion exchanger beads for each sample. The cation exchanger beads were pre-treated in 100 µl 1 M NaCl, 20 mM Citric Acid, pH 3.5 for 15 minutes. The beads were then washed 2× in 100 µl washing buffer (50 mM NaCl, 20 mM Citric Acid, 0.5% Tween 120, pH 3.5). The anion exchanger beads were pre-treated in 100 µl 1M NaCl, 20 mM Tris-HCl pH 10.0 for 15 minutes. The beads were then washed 2× in 100 µl washing buffer (50 mM NaCl, 20 mM Tris-HCl, 0.5% Tween 20, pH 3.5).

Cell Lysis and Ion Exchange

Anion/Cation Exchange (FIG. 9a):

Cell pellets were lysed in 500 µl lysis buffer (20 mM Tris, 1% Triton-x-100, 150 mM NaCl, 5 mM EDTA, pH 8) and incubated on a roller for 10 min at 4° C. The lysate was transferred to tubes containing pre-treated ion exchanger beads and incubated on a roller for 15 minutes at 4° C. The bead-protein complex was washed 3× in 20 mM Tris-HCl, 50 mM NaCl, pH 8.0. The proteins were eluted from the anion exchanger beads by adding 1M NaCl, 20 mM Citrate, pH 3.5, and incubating on a roller for 15 minutes. The proteins were eluted from the cation exchanger beads by adding 1 M NaCl, 20 mM Tris HCl pH 10.0 and incubating on a roller for 15 minutes. Analysed by SDS-PAGE.

Sample b (from Example 3, i.e. $5 \times 10^5$ cells):

Removed washing buffer from cells. The rosetted cells were lysed in 300 µl lysis buffer (20 mM Citric Acid, 50 mM NaCl, 20 mM Tris, 1% Triton-x-100, 5 mM EDTA, pH 3.5). Incubated on a roller at 4° C. for 15 minutes. Transferred the lysate to a new tube, containing pre-treated cation exchanger beads. Incubated on a roller at 4° C. for 15 minutes. Washed the beads 3× in 300 µl washing buffer (20 mM Citric Acid, 50 mM NaCl, 0.5% Tween 20, pH 3.5).

Resuspended beads in 100 µl elution buffer (20 mM Tris HCl, 1 M NaCl, pH 10.0) and incubated on a roller for 15 minutes. Eluted proteins were transferred to a new tube and analysed by SDS-PAGE.

Figure 9A:
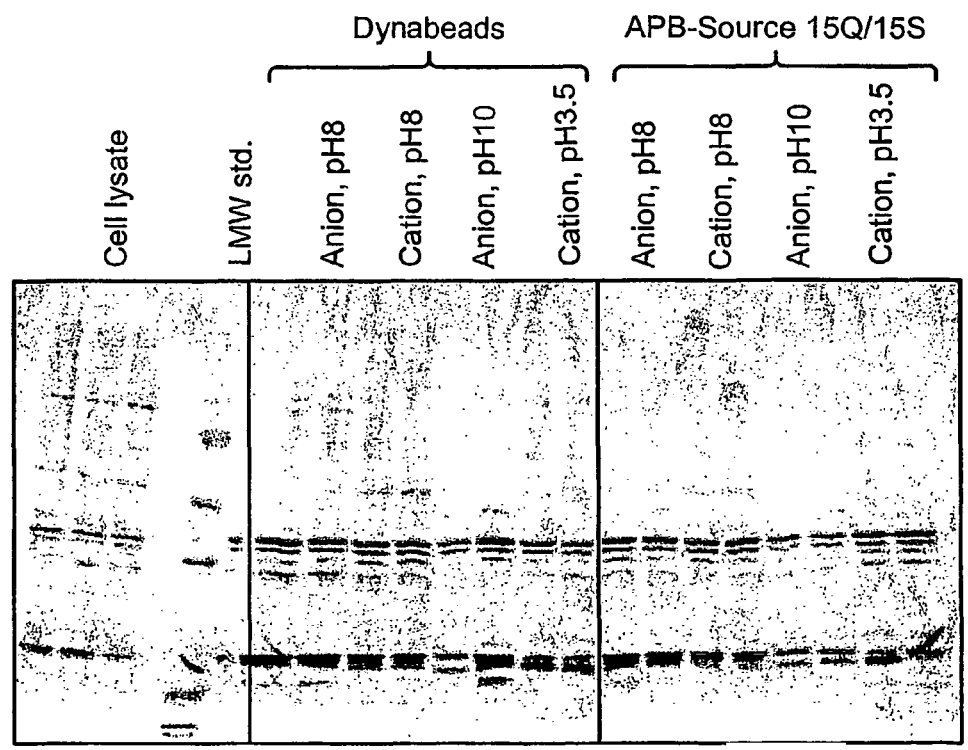
FIG. 9a shows the results for protein isolated using ion exchanger beads from a cell lysate comparing Dynabeads ion exchanger prototypes with AP-Biotechs 15 Q/S ion exchange resins.
Figure 9B:
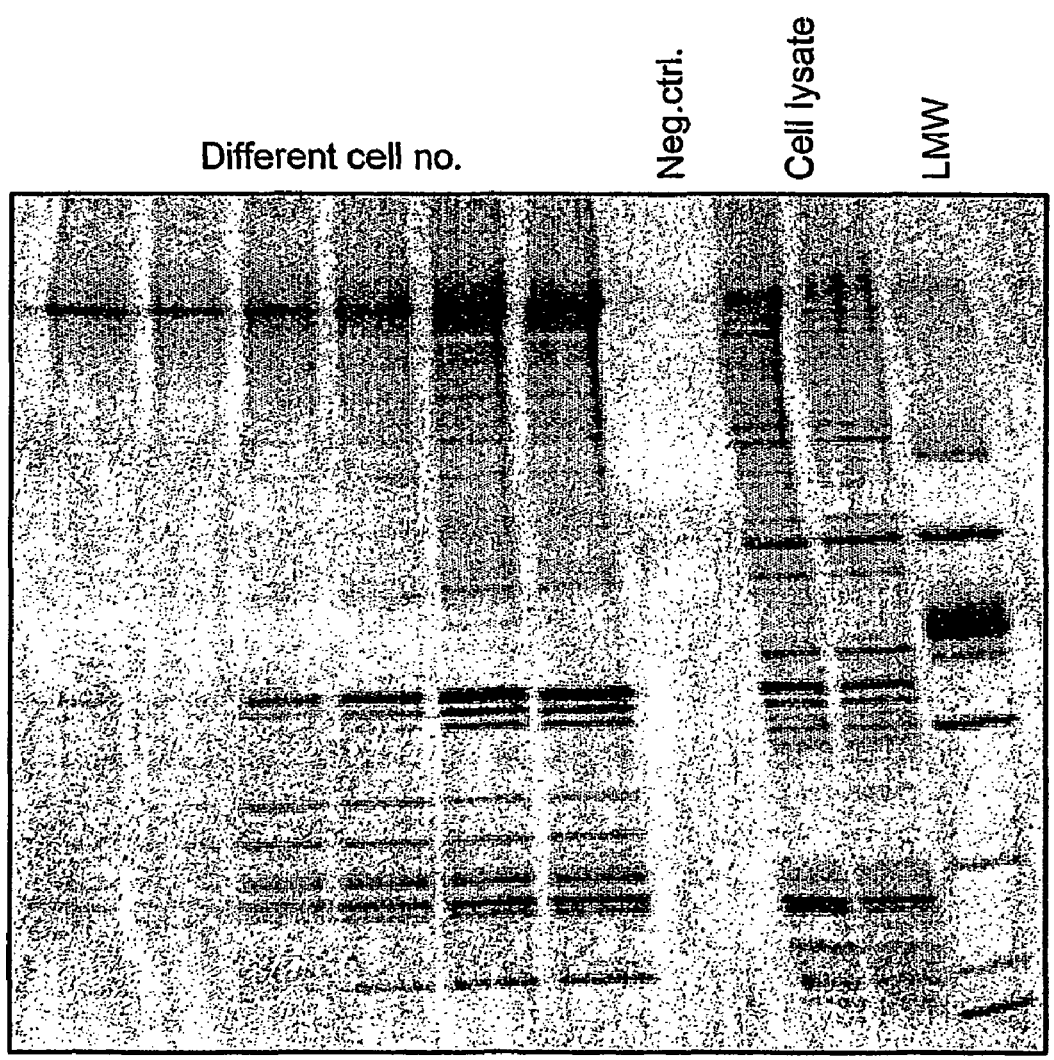
FIG. 9b shows the results for protein isolated from different numbers of carcinoma cells using the cation exchanger prototype beads.

The ion exchanger Dynabeads gave similar results for protein isolation as Amersham Pharmacia Biotech, ion exchangers (FIG. 9a). Protein fractionation was also carried out using cation exchanger beads from spiked carcinoma cells and compared to the cell lysate directly. FIG. 9b shows the results from this, where the negative control shows the unspecific background from unspiked blood.

EXAMPLE 5

Figure 10A:
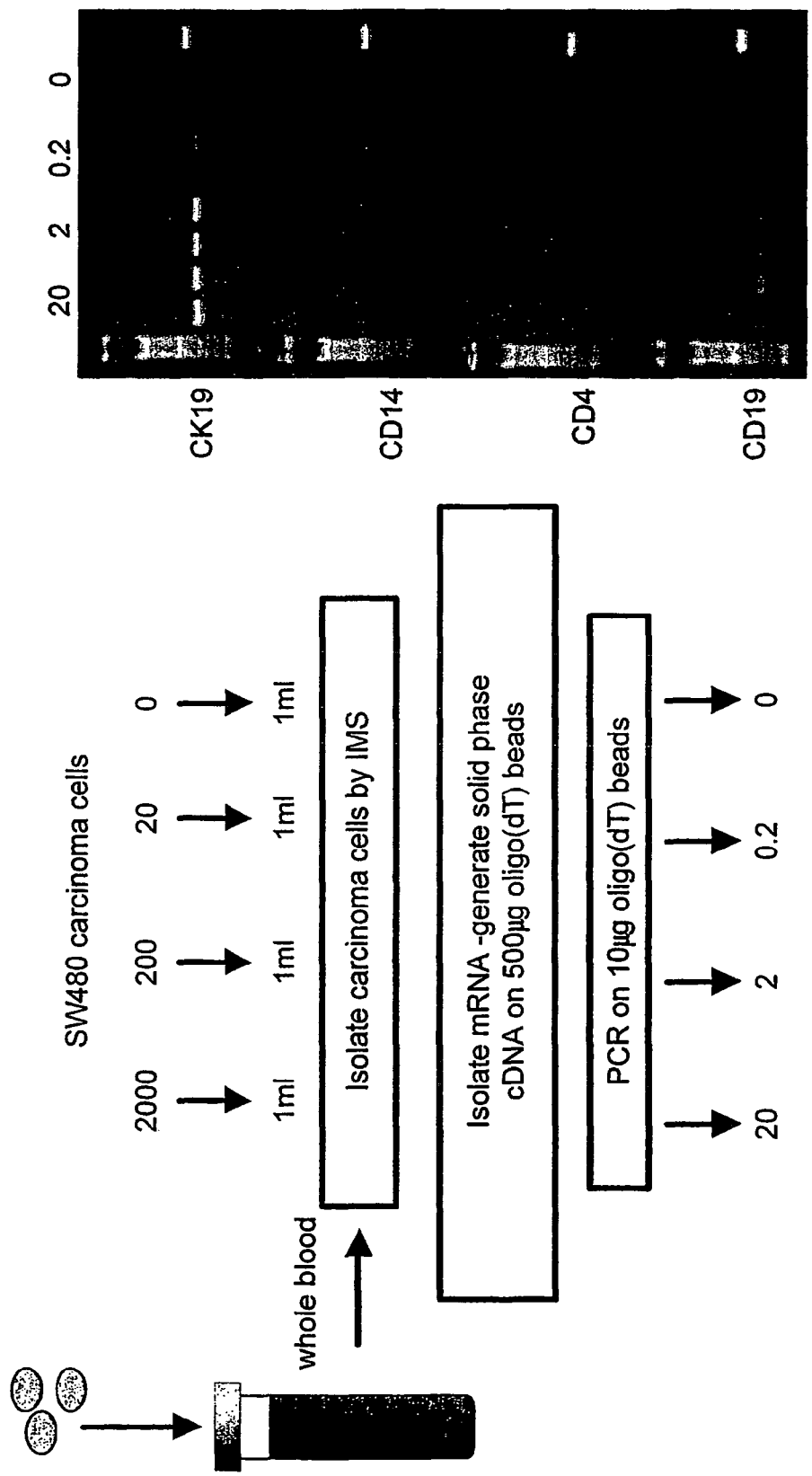
FIG. 10a shows PCR results for CK19, CD14, CD4 and CD19 for IMS isolated carcinoma cells, where 2000, 200 or 20 cells were spiked into whole blood. CK19 was detected in samples which only represented mRNA from 20, 2 or 0.2 cells.

Scaling Down the Techniques to Isolate Reduced Numbers of Cells 2000, 200 and 20 carcinoma cells were spiked into 1 ml of whole blood. The cell isolation was carried out as described in Example 3 and mRNA was obtained (using 500 µg oligo (dT) beads). cDNA was synthesised on the oligo (dT) beads using the same amount of beads as in previous experiments. PCR was carried out for these samples using CK19, CD14, CD4 and CD19 primers. Analysis was carried out on samples representing mRNA from 20, 2 and 0.2 cells. (FIG. 10a). It can be seen that all samples gave positive results for CK19, indicating the presence of carcinoma cells. The results for CD14 and CD4 were negative and low levels of CD19 were detected indicating again the very low levels of unspecific binding for IMS. Therefore 20 cells could easily be isolated and detected by this method.

The experiment was then repeated by spiking whole blood with 1, 5 and 10 carcinoma cells, where single cells had been picked with a micromanipulator. The cells were isolated as previously described, mRNA was isolated using less oligo (dT) beads (100 µg) and a solid phase cDNA library was generated as before. PCR was then carried out using the whole library from each isolation in one reaction with CK19 primers.

Figure 10B:
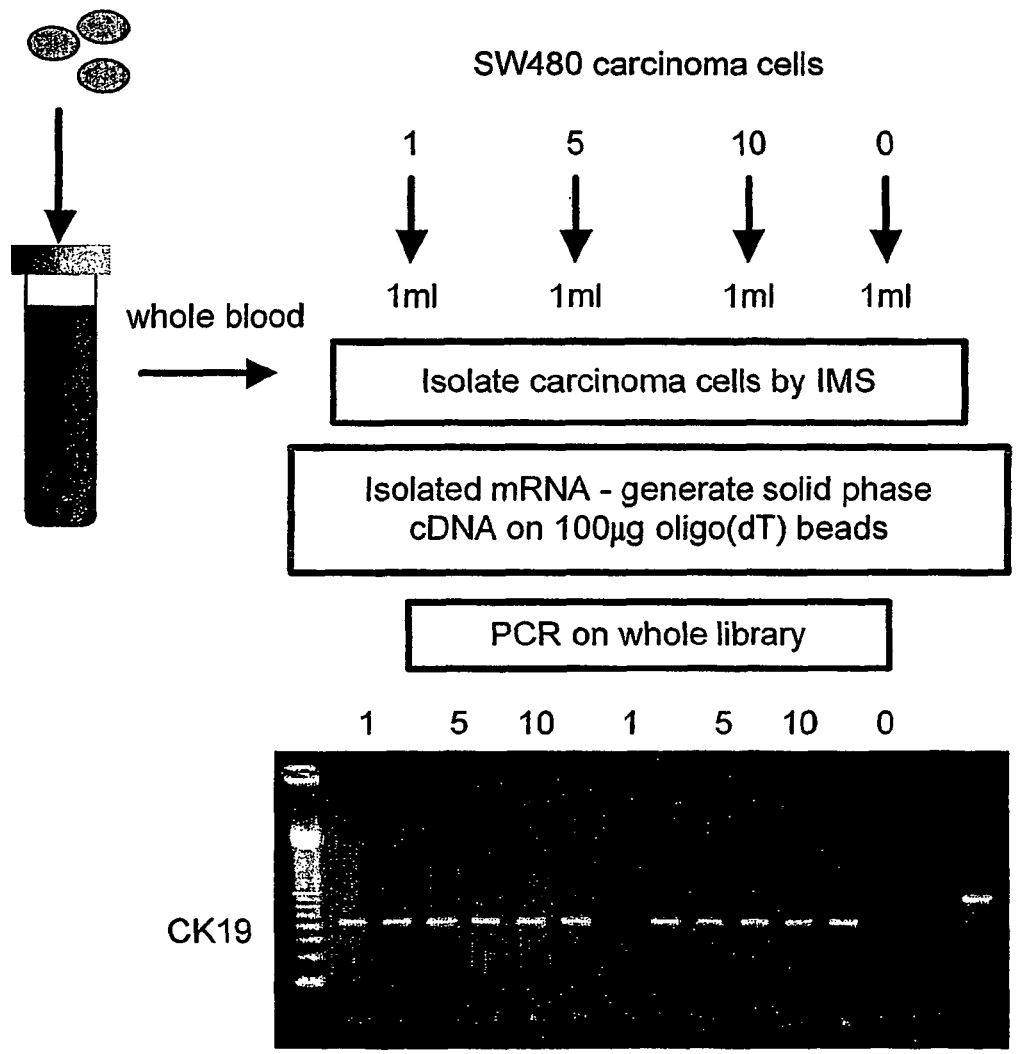
FIG. 10b shows PCR results for CK19 for IMS isolated carcinoma cells where 1, 5 or 10 cells were spiked into whole blood. CK19 was detected in one of two parallels for one cell.

FIG. 10b shows the results of these experiments, where the first 7 lanes show the MW-marker and then the results for unspiked cells (positive controls). The remaining lanes show the results for the spiked cells which were isolated. It can be seen that in one of two parallels, a single cell could be recovered from a spiked blood sample and detected using CK19 PCR.

Figure 11:
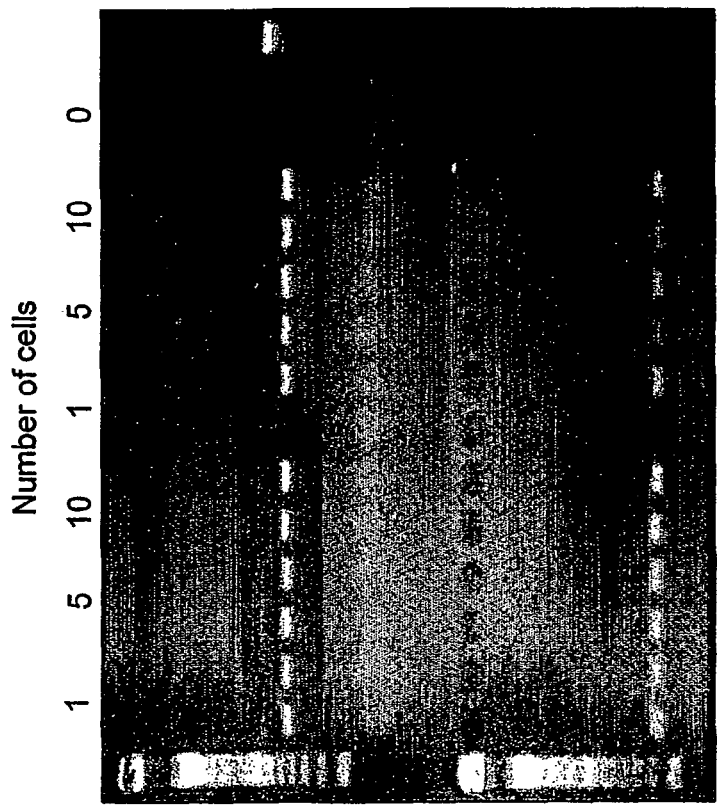
FIG. 11 shows the re-use of the solid phase cDNA library generated from down to one cell in PCR, detecting a second transcript from the same sample, demonstrating the flexibility and scalability of the methods.

This shows that the method described here is highly scalable. FIG. 11 shows the re-use of the cDNA libraries from FIG. 10b in a second PCR, detecting another transcript. The technology is also flexible and allows multiple mRNA analysis of single small samples.

The invention claimed is:

1. A method of isolating nucleic acid and protein from each other in a single sample, said method comprising:
   a) providing a sample that comprises nucleic acid components and protein components;
   b) contacting the sample with a plurality of magnetic particulate solid supports comprising:
      (i) contacting the sample of step b with a first magnetic particulate solid support under conditions wherein nucleic acid components bind to the first magnetic particulate solid supports in a sequence independent manner and the protein components remain substantially intact; and simultaneously
      (ii) contacting the sample of step b with a second magnetic particulate solid support distinct from the first magnetic particulate solid support, under conditions wherein protein components contained in the sample bind to the second magnetic particulate solid support through a chromatographic interaction and the nucleic acid components remain substantially intact; and
   c) separating the first magnetic particulate solid support to which are bound nucleic acid components and the second magnetic particulate solid supports to which are bound protein components from unbound components in the sample, thereby isolating nucleic acid components and protein components that are substantially intact; wherein the sample is not contacted with a chaotropic agent.

2. The method of claim 1, wherein the method comprises providing a sample that contains DNA and RNA components, and further comprises binding both DNA and RNA components to the first magnetic particulate solid support.

3. The method of claim 1, wherein the method comprises providing a sample that contains RNA components, and further comprises contacting the sample with a third magnetic particulate solid support, wherein the first, second and third magnetic particulate solid supports are distinct, and wherein RNA components bind to the third magnetic particulate solid support.

4. The method of claim 3, further comprising contacting the sample with the first magnetic particulate solid support and the third magnetic particulate solid support in separate steps.

5. The method of claim 3, further comprising isolating RNA components from the sample using an RNA-specified capture-probe carried by or attached to, or capable of binding to said first magnetic particulate solid support.

6. The method of claim 5, wherein said capture probe is or comprises a dT oligonucleotide or dU oligonucleotide.

7. The method of claim 1, wherein the method comprises isolating nucleic acid and protein components from the same sample.

8. The method of claim 1, wherein the method comprises providing a sample containing mRNA.

9. The method of claim 1, wherein the method comprises providing a sample containing genomic DNA.

10. The method of claim 1, wherein the method comprises isolating total RNA and/or the total DNA from the sample.

11. The method of claim 1, wherein the method comprises isolating the total nucleic acid component from the sample.

12. The method of claim 1, wherein the method comprises isolating the total protein component from the sample.

13. The method of claim 1, further comprising providing a sample selected from a food or allied product, and a clinical, environmental or biological sample.

14. The method of claim 1, further comprising subjecting the sample to a preliminary treatment step to free the nucleic acid and/or protein components from structures or entities in which they may be contained.

15. The method of claim 1, further comprising providing a sample that comprises one or more cell populations, and subjecting the sample to a cell isolation procedure prior to contacting said sample with said plurality of first and second magnetic particulate solid supports.

16. The method of claim 15, further comprising separately isolating one or more particular cell populations from the sample.

17. The method of claim 1 or claim 15, further comprising subjecting the sample, or a cell population isolated therefrom, to a cell lysis step prior to contacting said sample with said first magnetic solid particulate support, wherein the cell lysis step may be performed in the absence of a chaotropic agent.

18. The method of claim 17, further comprising subjecting the cell surface proteins of cells within or isolated from said sample to an in vitro modification procedure prior to the cell lysis step.

19. The method claim 17, further comprising subjecting the sample to a cell lysis step, wherein cell lysis and nucleic acid binding to the first magnetic particulate solid support occur simultaneously or concomitantly.

20. The method of claim 17 or 19, further comprising lysing the sample in the presence of a plurality of magnetic solid particles capable of binding cells, wherein the plurality of magnetic solid particles and the first magnetic particulate solid support are of different size.

21. The method of claim 1, wherein the sample is not divided at any stage of the method.

22. The method of claim 1, further comprising conducting a cell isolation, lysis, or preliminary treatment step conducted prior to contacting the sample with the first magnetic particulate solid support, and dividing the sample after the cell isolation, lysis, and/or preliminary treatment step.

23. The method of claim 1, wherein said sample is contacted with said plurality of magnetic particulate solid supports sequentially or simultaneously.

24. The method of claim 23, wherein in a first step DNA is isolated from said sample, in a second step RNA is isolated from said sample and in a third step, protein is isolated from said sample, and wherein said steps may be performed in any order.

25. The method of claim 1, further comprising isolating DNA components on the first magnetic particulate solid support selected from supports carrying surface carboxyl or hydroxyl groups, silica or silica-based supports, and supports having a polyamine coated surface.

26. The method of claim 1, further comprising binding nucleic acid components from the sample to the plurality of first magnetic particulate solid support in the presence of a detergent.

27. The method of claim 1, wherein the first magnetic particulate solid support has a positive or negative surface charge.

28. The method of claim 1, further comprising contacting the sample with the first magnetic particulate solid support in the presence of a plurality of solid magnetic particles, wherein the plurality of first magnetic particulate solid supports and the plurality of solid magnetic particles are of different size.

* * * * *